United States Patent

Biberger

(10) Patent No.: US 9,023,754 B2
(45) Date of Patent: *May 5, 2015

(54) NANO-SKELETAL CATALYST

(71) Applicant: SDCmaterials, Inc., Tempe, AZ (US)

(72) Inventor: Maximilian A. Biberger, Scottsdale, AZ (US)

(73) Assignee: SDCmaterials, Inc., Tempe, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/954,614

(22) Filed: Jul. 30, 2013

(65) Prior Publication Data

US 2013/0316896 A1  Nov. 28, 2013

Related U.S. Application Data

(63) Continuation of application No. 12/152,109, filed on May 9, 2008, now Pat. No. 8,524,631.

(60) Provisional application No. 60/928,946, filed on May 11, 2007.

(51) Int. Cl.
| | |
|---|---|
| *B01J 23/755* | (2006.01) |
| *B01J 23/745* | (2006.01) |
| *B01J 23/75* | (2006.01) |
| *B01J 23/74* | (2006.01) |
| *B01J 23/80* | (2006.01) |

(Continued)

(52) U.S. Cl.
CPC ............... *B01J 19/0013* (2013.01); *B22F 9/12* (2013.01); *B22F 2999/00* (2013.01); *F28D 7/024* (2013.01); *F28D 7/08* (2013.01); *F28D 15/00* (2013.01); *F28F 27/00* (2013.01); *Y10S 623/92* (2013.01); *Y10S 623/923* (2013.01); *B01J 25/00* (2013.01); *B01J 25/02* (2013.01)

(58) Field of Classification Search
None
See application file for complete search history.

(56) References Cited

U.S. PATENT DOCUMENTS

| | | | |
|---|---|---|---|
| 2,021,936 A | 11/1935 | Johnstone | |
| 2,284,554 A | 5/1942 | Beyerstedt | |

(Continued)

FOREIGN PATENT DOCUMENTS

| | | |
|---|---|---|
| CN | 101301610 A | 11/2008 |
| DE | 34 45 273 A1 | 6/1986 |

(Continued)

OTHER PUBLICATIONS

Babin, A. et al. (1985). "Solvents Used in the Arts," *Center for Safety in the Arts*: 16 pages.

(Continued)

*Primary Examiner* — Stanley Silverman
*Assistant Examiner* — Daniel Berns
(74) *Attorney, Agent, or Firm* — Morrison & Foerster LLP

(57) ABSTRACT

A method of producing a catalyst material with nano-scale structure, the method comprising: introducing a starting powder into a nano-powder production reactor, the starting powder comprising a catalyst material; the nano-powder production reactor nano-sizing the starting powder, thereby producing a nano-powder from the starting powder, the nano-powder comprising a plurality of nano-particles, each nano-particle comprising the catalyst material; and forming a catalyst precursor material from the nano-powder, wherein the catalyst precursor material is a densified bulk porous structure comprising the catalyst material, the catalyst material having a nano-scale structure.

34 Claims, 5 Drawing Sheets

(51) Int. Cl.
   *B01J 19/00* (2006.01)
   *B22F 9/12* (2006.01)
   *F28D 15/00* (2006.01)
   *F28F 27/00* (2006.01)
   *B01J 25/00* (2006.01)
   *B01J 25/02* (2006.01)
   *F28D 7/02* (2006.01)
   *F28D 7/08* (2006.01)

(56) References Cited

U.S. PATENT DOCUMENTS

| | | |
|---|---|---|
| 2,419,042 A | 4/1947 | Todd |
| 2,519,531 A | 8/1950 | Worn |
| 2,562,753 A | 7/1951 | Trost |
| 2,689,780 A | 9/1954 | Rice |
| 3,001,402 A | 9/1961 | Koblin |
| 3,042,511 A | 7/1962 | Reding, Jr. |
| 3,067,025 A | 12/1962 | Chisholm |
| 3,145,287 A | 8/1964 | Siebein et al. |
| 3,178,121 A | 4/1965 | Wallace, Jr. |
| 3,179,782 A | 4/1965 | Matvay |
| 3,181,947 A | 5/1965 | Vordahl |
| 3,235,700 A | 2/1966 | Mondain-Monval et al. |
| 3,313,908 A | 4/1967 | Unger et al. |
| 3,387,110 A | 6/1968 | Wendler et al. |
| 3,401,465 A | 9/1968 | Larwill |
| 3,450,926 A | 6/1969 | Kiernan |
| 3,457,788 A | 7/1969 | Miyajima |
| 3,537,513 A | 11/1970 | Austin |
| 3,552,653 A | 1/1971 | Inoue |
| 3,617,358 A | 11/1971 | Dittrich |
| 3,667,111 A | 6/1972 | Chartet |
| 3,741,001 A | 6/1973 | Fletcher et al. |
| 3,752,172 A | 8/1973 | Cohen et al. |
| 3,761,360 A | 9/1973 | Auvil et al. |
| 3,774,442 A | 11/1973 | Gustaysson |
| 3,804,034 A | 4/1974 | Stiglich, Jr. |
| 3,830,756 A | 8/1974 | Sanchez et al. |
| 3,871,448 A | 3/1975 | Vann et al. |
| 3,892,882 A | 7/1975 | Guest et al. |
| 3,914,573 A | 10/1975 | Muehlberger |
| 3,959,094 A | 5/1976 | Steinberg |
| 3,959,420 A | 5/1976 | Geddes et al. |
| 3,969,482 A | 7/1976 | Teller |
| 4,008,620 A | 2/1977 | Narato et al. |
| 4,018,388 A | 4/1977 | Andrews |
| 4,021,021 A | 5/1977 | Hall et al. |
| 4,127,760 A | 11/1978 | Meyer et al. |
| 4,139,497 A | 2/1979 | Castor et al. |
| 4,146,654 A | 3/1979 | Guyonnet |
| 4,157,316 A | 6/1979 | Thompson et al. |
| 4,171,288 A | 10/1979 | Keith et al. |
| 4,174,298 A | 11/1979 | Antos |
| 4,189,925 A | 2/1980 | Long |
| 4,227,928 A | 10/1980 | Wang |
| 4,248,387 A | 2/1981 | Andrews |
| 4,253,917 A | 3/1981 | Wang |
| 4,260,649 A | 4/1981 | Dension et al. |
| 4,284,609 A | 8/1981 | deVries |
| 4,315,874 A | 2/1982 | Ushida et al. |
| 4,326,492 A | 4/1982 | Leibrand, Sr. et al. |
| 4,344,779 A | 8/1982 | Isserlis |
| 4,369,167 A | 1/1983 | Weir |
| 4,388,274 A | 6/1983 | Rourke et al. |
| 4,419,331 A | 12/1983 | Montalvo |
| 4,431,750 A | 2/1984 | McGinnis et al. |
| 4,436,075 A | 3/1984 | Campbell et al. |
| 4,440,733 A | 4/1984 | Lawson et al. |
| 4,458,138 A | 7/1984 | Adrian et al. |
| 4,459,327 A | 7/1984 | Wang |
| 4,505,945 A | 3/1985 | Dubust et al. |
| 4,506,136 A | 3/1985 | Smyth et al. |
| 4,513,149 A | 4/1985 | Gray et al. |
| 4,523,981 A | 6/1985 | Ang et al. |
| 4,545,872 A | 10/1985 | Sammells et al. |
| RE32,244 E | 9/1986 | Andersen |
| 4,609,441 A | 9/1986 | Frese, Jr. et al. |
| 4,610,857 A | 9/1986 | Ogawa et al. |
| 4,616,779 A | 10/1986 | Serrano et al. |
| 4,723,589 A | 2/1988 | Iyer et al. |
| 4,731,517 A | 3/1988 | Cheney |
| 4,751,021 A | 6/1988 | Mollon et al. |
| 4,764,283 A | 8/1988 | Ashbrook et al. |
| 4,765,805 A | 8/1988 | Wahl et al. |
| 4,780,591 A | 10/1988 | Bernecki et al. |
| 4,824,624 A | 4/1989 | Palicka et al. |
| 4,836,084 A | 6/1989 | Vogelesang et al. |
| 4,855,505 A | 8/1989 | Koll |
| 4,866,240 A | 9/1989 | Webber |
| 4,877,937 A | 10/1989 | Müller |
| 4,885,038 A | 12/1989 | Anderson et al. |
| 4,921,586 A | 5/1990 | Molter |
| 4,970,364 A | 11/1990 | Müller |
| 4,982,050 A | 1/1991 | Gammie et al. |
| 4,983,555 A | 1/1991 | Roy et al. |
| 4,987,033 A | 1/1991 | Abkowitz et al. |
| 5,006,163 A | 4/1991 | Benn et al. |
| 5,015,863 A | 5/1991 | Takeshima et al. |
| 5,041,713 A | 8/1991 | Weidman |
| 5,043,548 A | 8/1991 | Whitney et al. |
| 5,070,064 A | 12/1991 | Hsu et al. |
| 5,073,193 A | 12/1991 | Chaklader et al. |
| 5,133,190 A | 7/1992 | Abdelmalek |
| 5,151,296 A | 9/1992 | Tokunaga |
| 5,157,007 A | 10/1992 | Domesle et al. |
| 5,192,130 A | 3/1993 | Endo et al. |
| 5,217,746 A | 6/1993 | Lenling et al. |
| 5,225,656 A | 7/1993 | Frind |
| 5,230,844 A | 7/1993 | Macaire et al. |
| 5,233,153 A | 8/1993 | Coats |
| 5,269,848 A | 12/1993 | Nakagawa |
| 5,294,242 A | 3/1994 | Zurecki et al. |
| 5,330,945 A | 7/1994 | Beckmeyer et al. |
| 5,338,716 A | 8/1994 | Triplett et al. |
| 5,369,241 A | 11/1994 | Taylor et al. |
| 5,371,049 A | 12/1994 | Moffett et al. |
| 5,372,629 A | 12/1994 | Anderson et al. |
| 5,392,797 A | 2/1995 | Welch |
| 5,436,080 A | 7/1995 | Inoue et al. |
| 5,439,865 A | 8/1995 | Abe et al. |
| 5,442,153 A | 8/1995 | Marantz et al. |
| 5,452,854 A | 9/1995 | Keller |
| 5,460,701 A | 10/1995 | Parker et al. |
| 5,464,458 A | 11/1995 | Yamamoto |
| 5,485,941 A | 1/1996 | Guyomard et al. |
| 5,486,675 A | 1/1996 | Taylor et al. |
| 5,534,149 A | 7/1996 | Birkenbeil et al. |
| 5,534,270 A | 7/1996 | De Castro |
| 5,543,173 A | 8/1996 | Horn, Jr. et al. |
| 5,553,507 A | 9/1996 | Basch et al. |
| 5,558,771 A | 9/1996 | Hagen et al. |
| 5,562,966 A | 10/1996 | Clarke et al. |
| 5,582,807 A | 12/1996 | Liao et al. |
| 5,596,973 A | 1/1997 | Grice |
| 5,611,896 A | 3/1997 | Swanepoel et al. |
| 5,630,322 A | 5/1997 | Heilmann et al. |
| 5,652,304 A | 7/1997 | Calderon et al. |
| 5,714,644 A | 2/1998 | Irgang et al. |
| 5,723,027 A | 3/1998 | Serole |
| 5,723,187 A | 3/1998 | Popoola et al. |
| 5,726,414 A | 3/1998 | Kitahashi et al. |
| 5,733,662 A | 3/1998 | Bogachek |
| 5,749,938 A | 5/1998 | Coombs |
| 5,776,359 A | 7/1998 | Schultz et al. |
| 5,788,738 A | 8/1998 | Pirzada et al. |
| 5,804,155 A | 9/1998 | Farrauto et al. |
| 5,811,187 A | 9/1998 | Anderson et al. |
| 5,837,959 A | 11/1998 | Muehlberger et al. |
| 5,851,507 A | 12/1998 | Pirzada et al. |
| 5,853,815 A | 12/1998 | Muehlberger |
| 5,858,470 A | 1/1999 | Bernecki et al. |
| 5,884,473 A | 3/1999 | Noda et al. |
| 5,905,000 A | 5/1999 | Yadav et al. |

(56) References Cited

U.S. PATENT DOCUMENTS

| | | |
|---|---|---|
| 5,928,806 A | 7/1999 | Olah et al. |
| 5,935,293 A | 8/1999 | Detering et al. |
| 5,973,289 A | 10/1999 | Read et al. |
| 5,989,648 A | 11/1999 | Phillips |
| 5,993,967 A | 11/1999 | Brotzman, Jr. et al. |
| 5,993,988 A | 11/1999 | Ohara et al. |
| 6,004,620 A | 12/1999 | Camm |
| 6,012,647 A | 1/2000 | Ruta et al. |
| 6,033,781 A | 3/2000 | Brotzman, Jr. et al. |
| 6,045,765 A | 4/2000 | Nakatsuji et al. |
| 6,059,853 A | 5/2000 | Coombs |
| 6,066,587 A | 5/2000 | Kurokawa et al. |
| 6,084,197 A | 7/2000 | Fusaro, Jr. |
| 6,093,306 A | 7/2000 | Hanrahan et al. |
| 6,093,378 A | 7/2000 | Deeba et al. |
| 6,102,106 A | 8/2000 | Manning et al. |
| 6,117,376 A | 9/2000 | Merkel |
| 6,140,539 A | 10/2000 | Sander et al. |
| 6,168,694 B1 | 1/2001 | Huang et al. |
| 6,190,627 B1 | 2/2001 | Hoke et al. |
| 6,213,049 B1 | 4/2001 | Yang |
| 6,214,195 B1 | 4/2001 | Yadav et al. |
| 6,228,904 B1 | 5/2001 | Yadav et al. |
| 6,254,940 B1 | 7/2001 | Pratsinis et al. |
| 6,261,484 B1 | 7/2001 | Phillips et al. |
| 6,267,864 B1 | 7/2001 | Yadav et al. |
| 6,322,756 B1 | 11/2001 | Arno et al. |
| 6,342,465 B1 | 1/2002 | Klein et al. |
| 6,344,271 B1 | 2/2002 | Yadav et al. |
| 6,362,449 B1 | 3/2002 | Hadidi et al. |
| 6,379,419 B1 | 4/2002 | Celik et al. |
| 6,387,560 B1 | 5/2002 | Yadav et al. |
| 6,395,214 B1 | 5/2002 | Kear et al. |
| 6,398,843 B1 | 6/2002 | Tarrant |
| 6,399,030 B1 | 6/2002 | Nolan |
| 6,409,851 B1 | 6/2002 | Sethuram et al. |
| 6,413,781 B1 | 7/2002 | Geis et al. |
| 6,416,818 B1 | 7/2002 | Aikens et al. |
| RE37,853 E | 9/2002 | Detering et al. |
| 6,444,009 B1 | 9/2002 | Liu et al. |
| 6,475,951 B1 | 11/2002 | Domesle et al. |
| 6,488,904 B1 | 12/2002 | Cox et al. |
| 6,506,995 B1 | 1/2003 | Fusaro, Jr. et al. |
| 6,517,800 B1 | 2/2003 | Cheng et al. |
| 6,524,662 B2 | 2/2003 | Jang et al. |
| 6,531,704 B2 | 3/2003 | Yadav et al. |
| 6,548,445 B1 | 4/2003 | Buysch et al. |
| 6,554,609 B2 | 4/2003 | Yadav et al. |
| 6,562,304 B1 | 5/2003 | Mizrahi |
| 6,562,495 B2 | 5/2003 | Yadav et al. |
| 6,569,393 B1 | 5/2003 | Hoke et al. |
| 6,569,397 B1 | 5/2003 | Yadav et al. |
| 6,569,518 B2 | 5/2003 | Yadav et al. |
| 6,572,672 B2 | 6/2003 | Yadav et al. |
| 6,579,446 B1 | 6/2003 | Teran et al. |
| 6,596,187 B2 | 7/2003 | Coll et al. |
| 6,603,038 B1 | 8/2003 | Hagemeyer et al. |
| 6,607,821 B2 | 8/2003 | Yadav et al. |
| 6,610,355 B2 | 8/2003 | Yadav et al. |
| 6,623,559 B2 | 9/2003 | Huang |
| 6,635,357 B2 | 10/2003 | Moxson et al. |
| 6,641,775 B2 | 11/2003 | Vigliotti et al. |
| 6,652,822 B2 | 11/2003 | Phillips et al. |
| 6,652,967 B2 | 11/2003 | Yadav et al. |
| 6,669,823 B1 | 12/2003 | Sarkas et al. |
| 6,682,002 B2 | 1/2004 | Kyotani |
| 6,689,192 B1 | 2/2004 | Phillips et al. |
| 6,699,398 B1 | 3/2004 | Kim |
| 6,706,097 B2 | 3/2004 | Zomes |
| 6,706,660 B2 | 3/2004 | Park |
| 6,710,207 B2 | 3/2004 | Bogan, Jr. et al. |
| 6,713,176 B2 | 3/2004 | Yadav et al. |
| 6,716,525 B1 | 4/2004 | Yadav et al. |
| 6,744,006 B2 | 6/2004 | Johnson et al. |
| 6,746,791 B2 | 6/2004 | Yadav et al. |
| 6,772,584 B2 | 8/2004 | Chun et al. |
| 6,786,950 B2 | 9/2004 | Yadav et al. |
| 6,813,931 B2 | 11/2004 | Yadav et al. |
| 6,817,388 B2 | 11/2004 | Tsangaris et al. |
| 6,832,735 B2 | 12/2004 | Yadav et al. |
| 6,838,072 B1 | 1/2005 | Kong et al. |
| 6,841,509 B1 | 1/2005 | Hwang et al. |
| 6,855,410 B2 | 2/2005 | Buckley |
| 6,855,426 B2 | 2/2005 | Yadav |
| 6,855,749 B1 | 2/2005 | Yadav et al. |
| 6,858,170 B2 | 2/2005 | Van Thillo et al. |
| 6,886,545 B1 | 5/2005 | Holm |
| 6,891,319 B2 | 5/2005 | Dean et al. |
| 6,896,958 B1 | 5/2005 | Cayton et al. |
| 6,902,699 B2 | 6/2005 | Fritzemeier et al. |
| 6,916,872 B2 | 7/2005 | Yadav et al. |
| 6,919,065 B2 | 7/2005 | Zhou et al. |
| 6,919,527 B2 | 7/2005 | Boulos et al. |
| 6,933,331 B2 | 8/2005 | Yadav et al. |
| 6,972,115 B1 | 12/2005 | Ballard |
| 6,986,877 B2 | 1/2006 | Takikawa et al. |
| 6,994,837 B2 | 2/2006 | Boulos et al. |
| 7,007,872 B2 | 3/2006 | Yadav et al. |
| 7,022,305 B2 | 4/2006 | Drumm et al. |
| 7,052,777 B2 | 5/2006 | Brotzman, Jr. et al. |
| 7,073,559 B2 | 7/2006 | O'Larey et al. |
| 7,074,364 B2 | 7/2006 | Jähn et al. |
| 7,081,267 B2 | 7/2006 | Yadav |
| 7,101,819 B2 | 9/2006 | Rosenflanz et al. |
| 7,147,544 B2 | 12/2006 | Rosenflanz |
| 7,147,894 B2 | 12/2006 | Zhou et al. |
| 7,166,198 B2 | 1/2007 | Van Der Walt et al. |
| 7,166,663 B2 | 1/2007 | Cayton et al. |
| 7,172,649 B2 | 2/2007 | Conrad et al. |
| 7,172,790 B2 | 2/2007 | Koulik et al. |
| 7,178,747 B2 | 2/2007 | Yadav et al. |
| 7,208,126 B2 | 4/2007 | Musick et al. |
| 7,211,236 B2 | 5/2007 | Stark et al. |
| 7,217,407 B2 | 5/2007 | Zhang |
| 7,220,398 B2 | 5/2007 | Sutorik et al. |
| 7,255,498 B2 | 8/2007 | Bush et al. |
| 7,265,076 B2 | 9/2007 | Taguchi et al. |
| 7,282,167 B2 | 10/2007 | Carpenter |
| 7,307,195 B2 | 12/2007 | Polverejan et al. |
| 7,323,655 B2 | 1/2008 | Kim |
| 7,384,447 B2 | 6/2008 | Kodas et al. |
| 7,402,899 B1 | 7/2008 | Whiting et al. |
| 7,417,008 B2 | 8/2008 | Richards et al. |
| 7,494,527 B2 | 2/2009 | Jurewicz et al. |
| 7,507,495 B2 | 3/2009 | Wang et al. |
| 7,517,826 B2 | 4/2009 | Fujdala et al. |
| 7,534,738 B2 | 5/2009 | Fujdala et al. |
| 7,541,012 B2 | 6/2009 | Yeung et al. |
| 7,541,310 B2 | 6/2009 | Espinoza et al. |
| 7,557,324 B2 | 7/2009 | Nylen et al. |
| 7,572,315 B2 | 8/2009 | Boulos et al. |
| 7,576,029 B2 | 8/2009 | Saito et al. |
| 7,576,031 B2 | 8/2009 | Beutel et al. |
| 7,604,843 B1 | 10/2009 | Robinson et al. |
| 7,611,686 B2 | 11/2009 | Alekseeva et al. |
| 7,615,097 B2 | 11/2009 | McKechnie et al. |
| 7,618,919 B2 | 11/2009 | Shimazu et al. |
| 7,622,693 B2 | 11/2009 | Foret |
| 7,632,775 B2 | 12/2009 | Zhou et al. |
| 7,635,218 B1 | 12/2009 | Lott |
| 7,674,744 B2 | 3/2010 | Shiratori et al. |
| 7,678,419 B2 | 3/2010 | Kevwitch et al. |
| 7,704,369 B2 | 4/2010 | Olah et al. |
| 7,709,411 B2 | 5/2010 | Zhou et al. |
| 7,709,414 B2 | 5/2010 | Fujdala et al. |
| 7,745,367 B2 | 6/2010 | Fujdala et al. |
| 7,750,265 B2 | 7/2010 | Belashchenko et al. |
| 7,759,279 B2 | 7/2010 | Shiratori et al. |
| 7,759,281 B2 | 7/2010 | Kezuka et al. |
| 7,803,210 B2 | 9/2010 | Sekine et al. |
| 7,842,515 B2 | 11/2010 | Zou et al. |
| 7,851,405 B2 | 12/2010 | Wakamatsu et al. |
| 7,874,239 B2 | 1/2011 | Howland |
| 7,875,573 B2 | 1/2011 | Beutel et al. |

(56) References Cited

U.S. PATENT DOCUMENTS

| | | |
|---|---|---|
| 7,897,127 B2 | 3/2011 | Layman et al. |
| 7,902,104 B2 | 3/2011 | Kalck |
| 7,905,942 B1 | 3/2011 | Layman |
| 7,935,655 B2 | 5/2011 | Tolmachev |
| 8,051,724 B1 | 11/2011 | Layman et al. |
| 8,076,258 B1 | 12/2011 | Biberger |
| 8,080,494 B2 | 12/2011 | Yasuda et al. |
| 8,089,495 B2 | 1/2012 | Keller |
| 8,129,654 B2 | 3/2012 | Lee et al. |
| 8,142,619 B2 | 3/2012 | Layman et al. |
| 8,168,561 B2 | 5/2012 | Virkar |
| 8,173,572 B2 | 5/2012 | Feaviour |
| 8,211,392 B2 | 7/2012 | Grubert et al. |
| 8,258,070 B2 | 9/2012 | Fujdala et al. |
| 8,278,240 B2 | 10/2012 | Tange et al. |
| 8,294,060 B2 | 10/2012 | Mohanty et al. |
| 8,309,489 B2 | 11/2012 | Cuenya et al. |
| 8,349,761 B2 | 1/2013 | Xia et al. |
| 8,404,611 B2 | 3/2013 | Nakamura et al. |
| 8,524,631 B2 * | 9/2013 | Biberger ............ 502/329 |
| 8,557,727 B2 | 10/2013 | Yin et al. |
| 8,574,408 B2 | 11/2013 | Layman |
| 8,652,992 B2 | 2/2014 | Yin et al. |
| 8,669,202 B2 | 3/2014 | van den Hoek et al. |
| 8,679,433 B2 | 3/2014 | Yin et al. |
| 2001/0004009 A1 | 6/2001 | MacKelvie |
| 2001/0042802 A1 | 11/2001 | Youds |
| 2001/0055554 A1 | 12/2001 | Hoke et al. |
| 2002/0018815 A1 | 2/2002 | Sievers et al. |
| 2002/0068026 A1 | 6/2002 | Murrell et al. |
| 2002/0071800 A1 | 6/2002 | Hoke et al. |
| 2002/0079620 A1 | 6/2002 | DuBuis et al. |
| 2002/0100751 A1 | 8/2002 | Carr |
| 2002/0102674 A1 | 8/2002 | Anderson |
| 2002/0131914 A1 | 9/2002 | Sung |
| 2002/0143417 A1 | 10/2002 | Ito et al. |
| 2002/0168466 A1 | 11/2002 | Tapphorn et al. |
| 2002/0182735 A1 | 12/2002 | Kibby et al. |
| 2002/0183191 A1 | 12/2002 | Faber et al. |
| 2002/0192129 A1 | 12/2002 | Shamouilian et al. |
| 2003/0036786 A1 | 2/2003 | Duren et al. |
| 2003/0042232 A1 | 3/2003 | Shimazu |
| 2003/0047617 A1 | 3/2003 | Shanmugham et al. |
| 2003/0066800 A1 | 4/2003 | Saim et al. |
| 2003/0085663 A1 | 5/2003 | Horsky |
| 2003/0102099 A1 | 6/2003 | Yadav et al. |
| 2003/0108459 A1 | 6/2003 | Wu et al. |
| 2003/0110931 A1 | 6/2003 | Aghajanian et al. |
| 2003/0129098 A1 | 7/2003 | Endo et al. |
| 2003/0139288 A1 | 7/2003 | Cai et al. |
| 2003/0143153 A1 | 7/2003 | Boulos et al. |
| 2003/0172772 A1 | 9/2003 | Sethuram et al. |
| 2003/0223546 A1 | 12/2003 | McGregor et al. |
| 2004/0009118 A1 | 1/2004 | Phillips et al. |
| 2004/0023302 A1 | 2/2004 | Archibald et al. |
| 2004/0023453 A1 | 2/2004 | Xu et al. |
| 2004/0077494 A1 | 4/2004 | LaBarge et al. |
| 2004/0103751 A1 | 6/2004 | Joseph et al. |
| 2004/0109523 A1 | 6/2004 | Singh et al. |
| 2004/0119064 A1 | 6/2004 | Narayan et al. |
| 2004/0127586 A1 | 7/2004 | Jin et al. |
| 2004/0129222 A1 | 7/2004 | Nylen et al. |
| 2004/0166036 A1 | 8/2004 | Chen et al. |
| 2004/0167009 A1 | 8/2004 | Kuntz et al. |
| 2004/0176246 A1 | 9/2004 | Shirk et al. |
| 2004/0208805 A1 | 10/2004 | Fincke et al. |
| 2004/0213998 A1 | 10/2004 | Hearley et al. |
| 2004/0235657 A1 | 11/2004 | Xiao et al. |
| 2004/0238345 A1 | 12/2004 | Koulik et al. |
| 2004/0251017 A1 | 12/2004 | Pillion et al. |
| 2004/0251241 A1 | 12/2004 | Blutke et al. |
| 2005/0000321 A1 | 1/2005 | O'Larey et al. |
| 2005/0000950 A1 | 1/2005 | Schroder et al. |
| 2005/0066805 A1 | 3/2005 | Park et al. |
| 2005/0070431 A1 | 3/2005 | Alvin et al. |
| 2005/0077034 A1 | 4/2005 | King |
| 2005/0097988 A1 | 5/2005 | Kodas et al. |
| 2005/0106865 A1 | 5/2005 | Chung et al. |
| 2005/0133121 A1 | 6/2005 | Subramanian et al. |
| 2005/0153069 A1 | 7/2005 | Tapphorn et al. |
| 2005/0163673 A1 | 7/2005 | Johnson et al. |
| 2005/0199739 A1 | 9/2005 | Kuroda et al. |
| 2005/0211018 A1 | 9/2005 | Jurewicz et al. |
| 2005/0220695 A1 | 10/2005 | Abatzoglou et al. |
| 2005/0227864 A1 | 10/2005 | Sutorik et al. |
| 2005/0233380 A1 | 10/2005 | Pesiri et al. |
| 2005/0240069 A1 | 10/2005 | Polverejan et al. |
| 2005/0258766 A1 | 11/2005 | Kim |
| 2005/0274646 A1 | 12/2005 | Lawson et al. |
| 2005/0275143 A1 | 12/2005 | Toth |
| 2006/0043651 A1 | 3/2006 | Yamamoto et al. |
| 2006/0051505 A1 | 3/2006 | Kortshagen et al. |
| 2006/0068989 A1 | 3/2006 | Ninomiya et al. |
| 2006/0094595 A1 | 5/2006 | Labarge |
| 2006/0096393 A1 | 5/2006 | Pesiri |
| 2006/0105910 A1 | 5/2006 | Zhou et al. |
| 2006/0108332 A1 | 5/2006 | Belashchenko |
| 2006/0153728 A1 | 7/2006 | Schoenung et al. |
| 2006/0153765 A1 | 7/2006 | Pham-Huu et al. |
| 2006/0159596 A1 | 7/2006 | De La Veaux et al. |
| 2006/0166809 A1 | 7/2006 | Malek et al. |
| 2006/0211569 A1 | 9/2006 | Dang et al. |
| 2006/0213326 A1 | 9/2006 | Gollob et al. |
| 2006/0222780 A1 | 10/2006 | Gurevich et al. |
| 2006/0231525 A1 | 10/2006 | Asakawa et al. |
| 2007/0044513 A1 | 3/2007 | Kear et al. |
| 2007/0048206 A1 | 3/2007 | Hung et al. |
| 2007/0049484 A1 | 3/2007 | Kear et al. |
| 2007/0063364 A1 | 3/2007 | Hsiao et al. |
| 2007/0084308 A1 | 4/2007 | Nakamura et al. |
| 2007/0084834 A1 | 4/2007 | Hanus et al. |
| 2007/0087934 A1 | 4/2007 | Martens et al. |
| 2007/0092768 A1 | 4/2007 | Lee et al. |
| 2007/0153390 A1 | 7/2007 | Nakamura et al. |
| 2007/0161506 A1 | 7/2007 | Saito et al. |
| 2007/0163385 A1 | 7/2007 | Takahashi et al. |
| 2007/0173403 A1 | 7/2007 | Koike et al. |
| 2007/0178673 A1 | 8/2007 | Gole et al. |
| 2007/0221404 A1 | 9/2007 | Das et al. |
| 2007/0253874 A1 | 11/2007 | Foret |
| 2007/0266825 A1 | 11/2007 | Ripley et al. |
| 2007/0292321 A1 | 12/2007 | Plischke et al. |
| 2008/0006954 A1 | 1/2008 | Yubuta et al. |
| 2008/0026041 A1 | 1/2008 | Tepper et al. |
| 2008/0031806 A1 | 2/2008 | Gavenonis et al. |
| 2008/0038578 A1 | 2/2008 | Li |
| 2008/0045405 A1 | 2/2008 | Beutel et al. |
| 2008/0047261 A1 | 2/2008 | Han et al. |
| 2008/0057212 A1 | 3/2008 | Dorier et al. |
| 2008/0064769 A1 | 3/2008 | Sato et al. |
| 2008/0104735 A1 | 5/2008 | Howland |
| 2008/0105083 A1 | 5/2008 | Nakamura et al. |
| 2008/0116178 A1 | 5/2008 | Weidman |
| 2008/0125308 A1 | 5/2008 | Fujdala et al. |
| 2008/0125313 A1 | 5/2008 | Fujdala et al. |
| 2008/0138651 A1 | 6/2008 | Doi et al. |
| 2008/0175936 A1 | 7/2008 | Tokita et al. |
| 2008/0187714 A1 | 8/2008 | Wakamatsu et al. |
| 2008/0206562 A1 | 8/2008 | Stucky et al. |
| 2008/0207858 A1 | 8/2008 | Kowaleski et al. |
| 2008/0248704 A1 | 10/2008 | Mathis et al. |
| 2008/0274344 A1 | 11/2008 | Vieth et al. |
| 2008/0277092 A1 | 11/2008 | Layman et al. |
| 2008/0277264 A1 | 11/2008 | Sprague |
| 2008/0277266 A1 | 11/2008 | Layman |
| 2008/0277267 A1 | 11/2008 | Biberger et al. |
| 2008/0277268 A1 | 11/2008 | Layman |
| 2008/0277269 A1 | 11/2008 | Layman et al. |
| 2008/0277270 A1 | 11/2008 | Biberger et al. |
| 2008/0277271 A1 | 11/2008 | Layman |
| 2008/0280049 A1 | 11/2008 | Kevwitch et al. |
| 2008/0280751 A1 | 11/2008 | Harutyunyan et al. |
| 2008/0283411 A1 | 11/2008 | Eastman et al. |
| 2008/0283498 A1 | 11/2008 | Yamazaki |

(56) References Cited

U.S. PATENT DOCUMENTS

| | | |
|---|---|---|
| 2008/0307960 A1 | 12/2008 | Hendrickson et al. |
| 2009/0010801 A1 | 1/2009 | Murphy et al. |
| 2009/0054230 A1 | 2/2009 | Veeraraghavan et al. |
| 2009/0081092 A1 | 3/2009 | Yang et al. |
| 2009/0088585 A1 | 4/2009 | Schammel et al. |
| 2009/0092887 A1 | 4/2009 | McGrath et al. |
| 2009/0098402 A1 | 4/2009 | Kang et al. |
| 2009/0114568 A1 | 5/2009 | Trevino et al. |
| 2009/0162991 A1 | 6/2009 | Beneyton et al. |
| 2009/0168506 A1 | 7/2009 | Han et al. |
| 2009/0170242 A1 | 7/2009 | Lin et al. |
| 2009/0181474 A1 | 7/2009 | Nagai |
| 2009/0200180 A1 | 8/2009 | Capote et al. |
| 2009/0208367 A1 | 8/2009 | Calio et al. |
| 2009/0209408 A1 | 8/2009 | Kitamura et al. |
| 2009/0223410 A1 | 9/2009 | Jun et al. |
| 2009/0253037 A1 | 10/2009 | Park et al. |
| 2009/0274897 A1 | 11/2009 | Kaner et al. |
| 2009/0274903 A1 | 11/2009 | Addiego |
| 2009/0286899 A1 | 11/2009 | Hofmann et al. |
| 2009/0324468 A1 | 12/2009 | Golden et al. |
| 2010/0050868 A1 | 3/2010 | Kuznicki et al. |
| 2010/0089002 A1 | 4/2010 | Merkel |
| 2010/0092358 A1 | 4/2010 | Koegel et al. |
| 2010/0124514 A1 | 5/2010 | Chelluri et al. |
| 2010/0166629 A1 | 7/2010 | Deeba |
| 2010/0180581 A1 | 7/2010 | Grubert et al. |
| 2010/0180582 A1 | 7/2010 | Mueller-Stach et al. |
| 2010/0186375 A1 | 7/2010 | Kazi et al. |
| 2010/0240525 A1 | 9/2010 | Golden et al. |
| 2010/0275781 A1 | 11/2010 | Tsangaris |
| 2010/0323118 A1 | 12/2010 | Mohanty et al. |
| 2011/0006463 A1 | 1/2011 | Layman |
| 2011/0030346 A1 | 2/2011 | Neubauer et al. |
| 2011/0049045 A1 | 3/2011 | Hurt et al. |
| 2011/0052467 A1 | 3/2011 | Chase et al. |
| 2011/0143041 A1 | 6/2011 | Layman et al. |
| 2011/0143915 A1 | 6/2011 | Yin et al. |
| 2011/0143916 A1 | 6/2011 | Leamon |
| 2011/0143926 A1 | 6/2011 | Yin et al. |
| 2011/0143930 A1 | 6/2011 | Yin et al. |
| 2011/0143933 A1 | 6/2011 | Yin et al. |
| 2011/0144382 A1 | 6/2011 | Yin et al. |
| 2011/0152550 A1 | 6/2011 | Grey et al. |
| 2011/0158871 A1 | 6/2011 | Arnold et al. |
| 2011/0174604 A1 | 7/2011 | Duesel et al. |
| 2011/0243808 A1 | 10/2011 | Fossey et al. |
| 2011/0245073 A1 | 10/2011 | Oljaca et al. |
| 2011/0247336 A9 | 10/2011 | Farsad et al. |
| 2011/0305612 A1 | 12/2011 | Müller-Stach et al. |
| 2012/0023909 A1 | 2/2012 | Lambert et al. |
| 2012/0045373 A1 | 2/2012 | Biberger |
| 2012/0063963 A1 | 3/2012 | Watanabe et al. |
| 2012/0097033 A1 | 4/2012 | Arnold et al. |
| 2012/0122660 A1 | 5/2012 | Andersen et al. |
| 2012/0124974 A1 | 5/2012 | Li et al. |
| 2012/0171098 A1 | 7/2012 | Hung et al. |
| 2012/0214666 A1 | 8/2012 | van den Hoek et al. |
| 2012/0308467 A1 | 12/2012 | Carpenter et al. |
| 2012/0313269 A1 | 12/2012 | Kear et al. |
| 2013/0079216 A1 | 3/2013 | Biberger et al. |
| 2013/0213018 A1 | 8/2013 | Yin et al. |
| 2013/0280528 A1 | 10/2013 | Biberger |
| 2013/0281288 A1 | 10/2013 | Biberger et al. |
| 2013/0316896 A1 | 11/2013 | Biberger |
| 2013/0331257 A1 | 12/2013 | Barcikowski et al. |
| 2013/0345047 A1 | 12/2013 | Biberger et al. |
| 2014/0018230 A1 | 1/2014 | Yin et al. |
| 2014/0120355 A1 | 5/2014 | Biberger |
| 2014/0128245 A1 | 5/2014 | Yin et al. |
| 2014/0140909 A1 | 5/2014 | Qi et al. |
| 2014/0148331 A1 | 5/2014 | Biberger et al. |
| 2014/0209451 A1 | 7/2014 | Biberger et al. |
| 2014/0228201 A1 | 8/2014 | Mendoza Gómez et al. |
| 2014/0243187 A1 | 8/2014 | Yin et al. |
| 2014/0249021 A1 | 9/2014 | van den Hoek et al. |
| 2014/0252270 A1 | 9/2014 | Lehman, Jr. |
| 2014/0263190 A1 | 9/2014 | Biberger et al. |
| 2014/0318318 A1 | 10/2014 | Layman et al. |

FOREIGN PATENT DOCUMENTS

| | | |
|---|---|---|
| EP | 0 347 386 A1 | 12/1989 |
| EP | 0 385 742 A1 | 9/1990 |
| EP | 1 134 302 A1 | 9/2001 |
| EP | 1 256 378 A2 | 11/2002 |
| EP | 1 619 168 A1 | 1/2006 |
| EP | 1 790 612 A1 | 5/2007 |
| EP | 1 955 765 A1 | 8/2008 |
| GB | 1 307 941 A | 2/1973 |
| JP | 49-31571 A | 3/1974 |
| JP | 56-146804 A | 11/1981 |
| JP | 61-086815 A | 5/1986 |
| JP | 62-102827 A | 5/1987 |
| JP | 63-214342 A | 9/1988 |
| JP | 1-164795 A | 6/1989 |
| JP | 2-6339 A | 1/1990 |
| JP | 3-226509 A | 10/1991 |
| JP | 5-193909 A | 8/1993 |
| JP | 05-228361 A | 9/1993 |
| JP | 05-324094 A | 12/1993 |
| JP | 6-93309 A | 4/1994 |
| JP | 6-135797 A | 5/1994 |
| JP | 6-172820 A | 6/1994 |
| JP | 6-272012 A | 9/1994 |
| JP | H6-065772 U | 9/1994 |
| JP | 07-031873 A | 2/1995 |
| JP | 7-138020 A | 5/1995 |
| JP | 7-207381 A | 8/1995 |
| JP | 07-256116 A | 10/1995 |
| JP | 8-158033 A | 6/1996 |
| JP | 8-215576 A | 8/1996 |
| JP | 8-217420 A | 8/1996 |
| JP | 9-141087 A | 6/1997 |
| JP | 10-130810 A | 5/1998 |
| JP | 10-249198 A | 9/1998 |
| JP | 11-502760 A | 3/1999 |
| JP | 2000-220978 A | 8/2000 |
| JP | 2002-88486 A | 3/2002 |
| JP | 2002-241812 A | 8/2002 |
| JP | 2002-336688 A | 11/2002 |
| JP | 2003-126694 A | 5/2003 |
| JP | 2004-233007 A | 8/2004 |
| JP | 2004-249206 A | 9/2004 |
| JP | 2004-290730 A | 10/2004 |
| JP | 2005-503250 A | 2/2005 |
| JP | 2005-122621 A | 5/2005 |
| JP | 2005-218937 A | 8/2005 |
| JP | 2005-342615 A | 12/2005 |
| JP | 2006-001779 A | 1/2006 |
| JP | 2006-508885 A | 3/2006 |
| JP | 2006-87965 A | 4/2006 |
| JP | 2006-247446 A | 9/2006 |
| JP | 2006-260385 A | 9/2006 |
| JP | 2006-326554 A | 12/2006 |
| JP | 2007-29859 A | 2/2007 |
| JP | 2007-44585 A | 2/2007 |
| JP | 2007-46162 A | 2/2007 |
| JP | 2007-138287 A | 6/2007 |
| JP | 2007-203129 A | 8/2007 |
| SU | 493241 A | 3/1976 |
| TW | 200611449 | 4/2006 |
| TW | 201023207 | 6/2010 |
| WO | WO-96/28577 A1 | 9/1996 |
| WO | WO-00/72965 A1 | 12/2000 |
| WO | WO-02/092503 A1 | 11/2002 |
| WO | WO-03/094195 A1 | 11/2003 |
| WO | WO-2004/052778 A2 | 6/2004 |
| WO | WO-2005/063390 A1 | 7/2005 |
| WO | WO 2006/079213 A1 | 8/2006 |
| WO | WO-2006/096205 A2 | 9/2006 |
| WO | WO-2007/144447 A1 | 12/2007 |
| WO | WO-2008/092478 A1 | 8/2008 |
| WO | WO-2008/130451 A2 | 10/2008 |

(56) References Cited

FOREIGN PATENT DOCUMENTS

| WO | WO-2008/130451 A3 | 10/2008 |
|---|---|---|
| WO | WO-2009/017479 A1 | 2/2009 |
| WO | WO-2011/081833 A1 | 7/2011 |
| WO | WO-2012/028695 A2 | 3/2012 |
| WO | WO-2013/028575 A1 | 2/2013 |

OTHER PUBLICATIONS

Bateman, J. E. et al. (Dec. 17, 1998). "Alkylation of Porous Silicon by Direct Reaction with Alkenes and Alkynes," *Angew. Chem Int. Ed.* 37(19):2683-2685.

Carrot, G. et al. (Sep. 17, 2002). "Surface-Initiated Ring-Opening Polymerization: A Versatile Method for Nanoparticle Ordering," *Macromolecules* 35(22):8400-8404.

Chen, H.-S. et al. (Jul. 3, 2001). "On the Photoluminescence of Si Nanoparticles," *Mater. Phys. Mech.* 4:62-66.

Chen, W.-J. et al. (Mar. 18, 2008). "Functional $Fe_3O_4/TiO_2$ Core/Shell Magnetic Nanoparticles as Photokilling Agents for Pathogenic Bacteria," *Small* 4(4): 485-491.

Faber, K. T. et al. (Sep. 1988). "Toughening by Stress-Induced Microcracking in Two-Phase Ceramics," *Journal of the American Ceramic Society* 71: C-399-C401.

Fauchais, P. et al. (Jun. 1989). "La Projection Par Plasma: Une Revue," *Ann. Phys. Fr.* 14(3):261-310.

Fauchais, P. et al. (Jan. 1993). "Les Dépôts Par Plasma Thermique," *Revue Générale De L'Electricité*, RGE, Paris, France, No. 2, pp. 7-12 (in French).

Fauchais, P. et al. (Jan. 1996). "Plasma Spray: Study of the Coating Generation," *Ceramics International* 22(4):295-303.

Fojtik, A. et al. (Apr. 29, 1994). "Luminescent Colloidal Silicon Particles,"*Chemical Physics Letters* 221:363-367.

Fojtik, A. (Jan. 13, 2006). "Surface Chemistry of Luminescent Colloidal Silicon Nanoparticles," *J. Phys. Chem. B.* 110(5):1994-1998.

Gangeri, M. et al. (2009). "Fe and Pt Carbon Nanotubes for the Electrocatalytic Conversion of Carbon Dioxide to Oxygenates," *Catalysis Today* 143: 57-63.

Gutsch, A. et al. (2002). "Gas-Phase Production of Nanoparticles," *Kona* No. 20, pp. 24-37.

Han, B. Q. et al. (Jan. 2004). "Deformation Mechanisms and Ductility of Nanostructured Al Alloys", *Mat. Res. Soc. Symp. Proc.* 821:p. 9.1.1-p. 9.1.6.

Heberlein, J. (2002). "New Approaches in Thermal Plasma Technology", *Pure Appl. Chem.* 74(3):327-335.

Hua, F. et al. (Mar. 2006). "Organically Capped Silicon Nanoparticles With Blue Photoluminescence Prepared by Hydrosilylation Followed by Oxidation," *Langmuir* 22(9):4363-4370.

Ji, Y. et al. (Nov. 2002) "Processing and Mechanical Properties of $Al_2O_3$-5 vol.% Cr Nanocomposites," *Journal of the European Ceramic Society* 22(12):1927-1936.

Jouet, R. J. et al. (Jan. 25, 2005). "Surface Passivation of Bare Aluminum Nanoparticles Using Perfluoroalkyl Carboxylic Acids," *Chem. Mater.*17(11):2987-2996.

Kenvin, J. C. et al. (1992). "Supported Catalysts Prepared from Mononuclear Copper Complexes: Catalytic Properties", *J. Catalysis* 135:81-91.

Konrad, H. et al. (1996). "Nanostructured Cu—Bi Alloys Prepared by Co-Evaporation in a Continuous Gas Flow," *NanoStructured Materials* 7(6):605-610.

Kim, N. Y. et al. (Mar. 5, 1997). "Thermal Derivatization of Porous Silicon with Alcohols," *J. Am. Chem. Soc.* 119(9):2297-2298.

Kwon, Y.-S. et al. (Apr. 30, 2003). "Passivation Process for Superfine Aluminum Powders Obtained by Electrical Explosion of Wires," *Applied Surface Science* 211:57-67.

Langner, A. et al. (Aug. 25, 2005). "Controlled Silicon Surface Functionalization by Alkene Hydrosilylation," *J. Am. Chem. Soc.* 127(37):12798-12799.

Li, D. et al. (Apr. 9, 2005). "Environmentally Responsive "Hairy" Nanoparticles: Mixed Homopolymer Brushes on Silica Nanoparticles Synthesized by Living Radical Polymerization Techniques," *J. Am. Chem. Soc.* 127(7):6248-6256.

Li, X. et al. (May 25, 2004). "Surface Functionalization of Silicon Nanoparticles Produced by Laser-Driven Pyrolysis of Silane Followed by HF—$HNO_3$ Etching," *Langmuir* 20(11):4720-4727.

Liao, Y.-C. et al. (Jun. 27, 2006). "Self-Assembly of Organic Monolayers on Aerosolized Silicon Nanoparticles," *J.Am. Chem. Soc.* 128(28):9061-9065.

Liu, S.-M. et al. (Jan. 13, 2006). "Enhanced Photoluminescence from Si Nano-Organosols by Functionalization With Alkenes and Their Size Evolution," *Chem. Mater.* 18(3):637-642.

Luo, J. et al. (2008). "Core/Shell Nanoparticles as Electrocatalysts for Fuel Cell Reactions," *Advanced Materials* 20: 4342-4347.

Mignard, D. et al. (2003). "Methanol Synthesis from Flue-Gas $CO_2$ and Renewable Electricity: A Feasibility Study," *International Journal of Hydrogen Energy* 28: 455-464.

Mühlenweg, H. et al. (2004). "Gas-Phase Reactions—Open Up New Roads to Nanoproducts," *Degussa ScienceNewsletter* No. 08, pp. 12-16.

Nagai, Y. et al. (Jul. 3, 2006). "Sintering Inhibition Mechanism of Platinum Supported on Ceria-Based Oxide and Pt-Oxide-Support Interaction," *J. Catalysis* 242:103-109.

NASA (2009). "Enthalpy," Article located at http://www.grc.nasa.gov/WWW/K-12/airplane/enthalpy.htrnl, published by National Aeronautics and Space Administration on Nov. 23, 2009, 1 page.

Neiner, D. (Aug. 5, 2006). "Low-Temperature Solution Route to Macroscopic Amounts of Hydrogen Terminated Silicon Nanoparticles," *J. Am. Chem. Soc.* 128:11016-11017.

Netzer, L. et al. (1983). "A New Approach to Construction of Artificial Monolayer Assemblies," *J. Am. Chem. Soc.* 105(3):674-676.

Park, H.-Y. et al. (May 30, 2007). "Fabrication of Magnetic Core@Shell Fe Oxide@Au Nanoparticles for Interfacial Bioactivity and Bio-Separation," *Langmuir* 23: 9050-9056.

Park, N.-G. et al. (Feb. 17, 2004). "Morphological and Photoelectrochemical Characterization of Core-Shell Nanoparticle Films for Dye-Sensitized Solar Cells: Zn—O Type Shell on $SnO_2$ and $TiO_2$ Cores," *Langmuir* 20: 4246-4253.

"Plasma Spray and Wire Flame Spray Product Group," located at http://www.processmaterials.com/spray.html, published by Process Materials, Inc., last accessed Aug. 5, 2013, 2 pages.

"Platinum Group Metals: Annual Review 1996" (Oct. 1997). Engineering and Mining Journal, p. 63.

Rahaman, R. A. et al. (1995). "Synthesis of Powders," in *Ceramic Processing and Sintering*. Marcel Decker, Inc., New York, pp. 71-77.

Sailor, M. J. (1997). "Surface Chemistry of Luminescent Silicon Nanocrystallites," *Adv. Mater.* 9(10):783-793.

Stiles, A. B. (Jan. 1, 1987). "Manufacture of Carbon-Supported Metal Catalysts," in *Catalyst Supports and Supported Catalysts*, Butterworth Publishers, MA, pp. 125-132.

Subramanian, S. et al. (1991). "Structure and Activity of Composite Oxide Supported Platinum-Iridium Catalysts," *Applied Catalysts* 74: 65-81.

Tao, Y.-T. (May 1993). "Structural Comparison of Self-Assembled Monolayers of *n*-Alkanoic Acids on the surfaces of Silver, Copper, and Aluminum," *J. Am. Chem. Soc.* 115(10):4350-4358.

Ünal, N. et al. (Nov. 2011). "Influence of WC Particles on the Microstructural and Mechanical Properties of 3 mol% $Y_2O_3$ Stabilized $ZrO_2$ Matrix Composites Produced by Hot Pressing," Journal of the European Ceramic Society (31)13: 2267-2275.

Vardelle, A. et al. (1996). "Coating Generation: Vaporization of Particles in Plasma Spraying and Splat Formation," Universite de Limoges, 123 Avenue A. Thomas 87000, Limoges, France, *Pure & Appl. Chem.* 68(5):1093-1099.

Vardelle, M. et al. (Jun. 1991). "Experimental Investigation of Powder Vaporization in Thermal Plasma Jets," *Plasma Chemistry and Plasma Processing* 11(2):185-201.

Yoshida, T. (1994). "The Future of Thermal Plasma Processing for Coating", *Pure & Appl. Chem.* 66(6):1223-1230.

Zou, J. et al. (Jun. 4, 2004). "Solution Synthesis of Ultrastable Luminescent Siloxane-Coated Silicon Nanoparticles," *Nano Letters* 4(7):1181-1186.

Notice of Allowance mailed on Oct. 27, 2009, for U.S. Appl. No. 12/151,932, filed May 8, 2008, for Kevwitch et al.

(56) References Cited

OTHER PUBLICATIONS

Final Office Action mailed on May 10, 2011, for U.S. Appl. No. 12/152,098, filed May 9, 2009, for Biberger et al., 14 pages.
U.S. Appl. No. 13/291,983, filed Nov. 8, 2011, for Layman et al.
U.S. Appl. No. 12/152,084, filed May 9, 2008, for Biberger.
U.S. Appl. No. 13/028,693, filed Feb. 16, 2011, for Biberger.
U.S. Appl. No. 12/943,909, filed Nov. 10, 2010, for Layman.
U.S. Appl. No. 12/152,111, filed May 9, 2008, for Biberger et al.
U.S. Appl. No. 12/151,830, filed May 8, 2008, for Biberger et al.
U.S. Appl. No. 12/968,248, filed Dec. 14, 2010, for Biberger.
U.S. Appl. No. 12/968,245, filed Dec. 14, 2010, for Biberger.
U.S. Appl. No. 12/968,241, filed Dec. 14, 2010, for Biberger.
U.S. Appl. No. 12/968,239, filed Dec. 14, 2010, for Biberger.
U.S. Appl. No. 12/969,128, filed Dec. 15, 2010, for Biberger.
U.S. Appl. No. 12/962,463, filed Dec. 7, 2010, for Leamon.
U.S. Appl. No. 12/961,030, filed Dec. 6, 2010, for Lehman.
U.S. Appl. No. 12/961,108, filed Dec. 6, 2010, for Lehman.
U.S. Appl. No. 12/961,200, filed Dec. 6, 2010, for Lehman.
U.S. Appl. No. 12/968,253, filed Dec. 14, 2010, for Biberger.
U.S. Appl. No. 12/968,235, filed Dec. 14, 2010, for Biberger.
U.S. Appl. No. 12/969,306, filed Dec. 15, 2010, for Lehman et al.
U.S. Appl. No. 12/969,447, filed Dec. 15, 2010, for Biberger et al.
U.S. Appl. No. 12/969,087, filed Dec. 15, 2010, for Biberger.
U.S. Appl. No. 12/962,533, filed Dec. 7, 2010, for Yin et al.
U.S. Appl. No. 12/962,523, filed Dec. 7, 2010, for Yin et al.
U.S. Appl. No. 12/001,643, filed Dec. 11, 2007, for Biberger et al.
U.S. Appl. No. 12/474,081, filed May 28, 2009, for Biberger et al.
U.S. Appl. No. 12/001,602, filed Dec. 11, 2007, for Biberger et al.
U.S. Appl. No. 12/001,644, filed Dec. 11, 2007, for Biberger et al.
U.S. Appl. No. 12/969,457, filed Nov. 15, 2010, for Leamon et al.
U.S. Appl. No. 12/969,503, filed Nov. 15, 2010, for Leamon et al.
U.S. Appl. No. 12/954,813, filed Nov. 26, 2010, for Biberger.
U.S. Appl. No. 12/954,822, filed Nov. 26, 2010, for Biberger.
U.S. Appl. No. 13/033,514, filed Feb. 23, 2011, for Biberger et al.
U.S. Appl. No. 13/589,024, filed Aug. 17, 2012, for Yin et al.
U.S. Appl. No. 13/801,726, filed Mar. 13, 2013, for Qi et al.
Ahmad, K. et al. (2008). "Hybrid Nanocomposites: A New Route Towards Tougher Alumina Ceramics," *Composites Science and Technology* 68: 1321-1327.
Chaim, R. et al. (2009). "Densification of Nanocrystalline $Y_2O_3$ Ceramic Powder by Spark Plasma Sintering," *Journal of European Ceramic Society* 29: 91-98.
Chau, J. K. H. et al. (2005). "Microwave Plasma Synthesis of Silver Nanopowders," *Materials Letters* 59: 905-908.
Das, N. et al. (2001). "Influence of the Metal Function in the "One-Pot" Synthesis of 4-Methyl-2-Pentanone (Methyl Isobutyl Ketone) from Acetone Over Palladium Supported on Mg(Al)O Mixed Oxides Catalysts," *Catalysis Letters* 71(3-4): 181-185.
Ihlein, G. et al.(1998). "Ordered Porous Materials as Media for the Organization of Matter on the Nanoscale," *Applied Organometallic Chemistry* 12: 305-314.
Lakis, R. E. et al. (1995). "Alumina-Supported Pt—Rh Catalysts: I. Microstructural Characterization," *Journal of Catalysis* 154: 261-275.
Schimpf, S. et al. (2002). "Supported Gold Nanoparticles: In-Depth Catalyst Characterization and Application in Hydrogenation and Oxidation Reactions," *Catalysis Today* 2592: 1-16.
Viswanathan, V. et al. (2006). "Challenges and Advances in Nanocomposite Processing Techniques," *Materials Science and Engineering* R 54: 121-285.
Wan, J. et al. (2005). "Spark Plasma Sintering of Silicon Nitride/ Silicon Carbide Nanocomposites with Reduced Additive Amounts," *Scripta Materialia* 53: 663-667.

\* cited by examiner

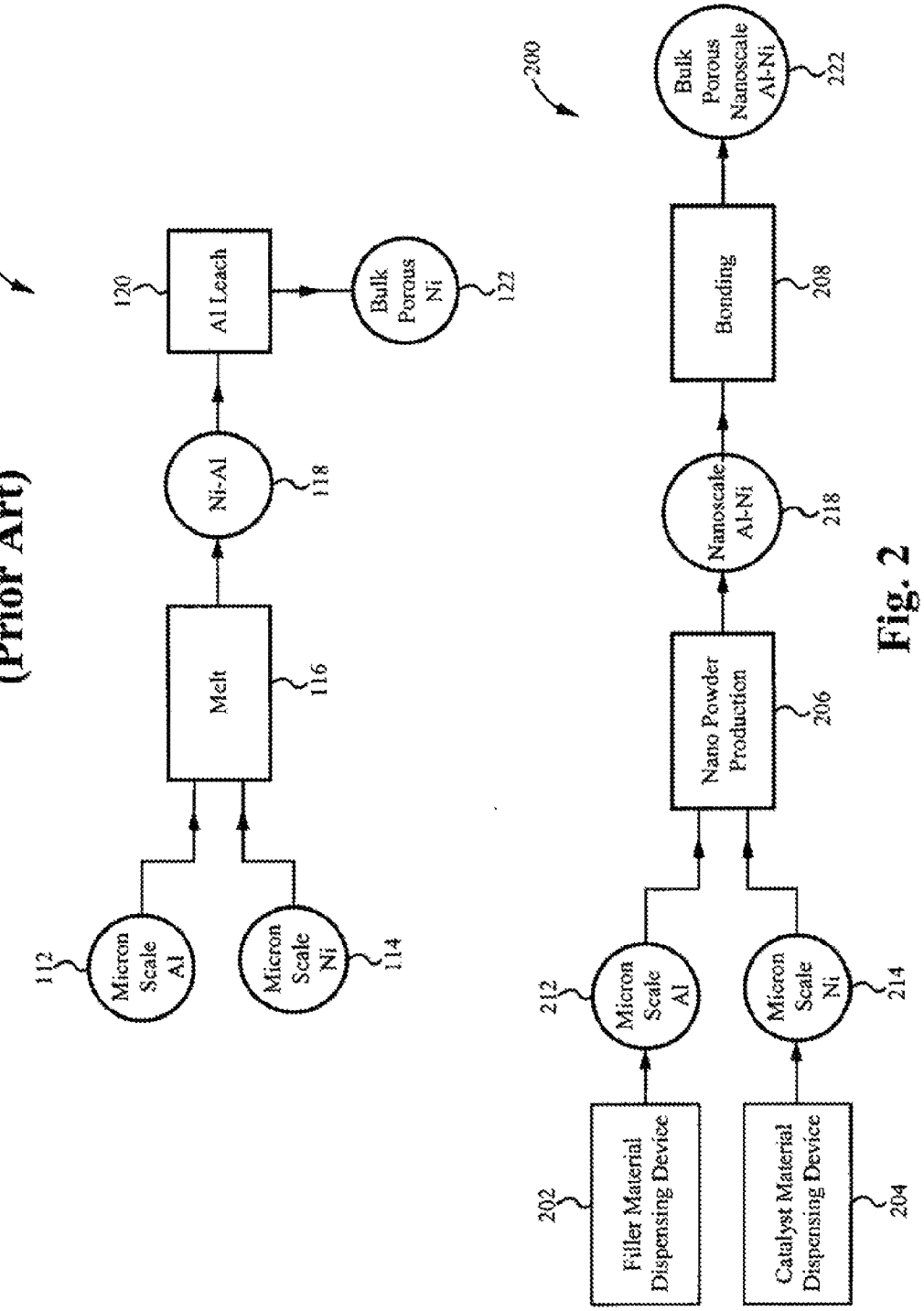

US 9,023,754 B2

NANO-SKELETAL CATALYST

CROSS-REFERENCE TO RELATED APPLICATIONS

This application is a continuation application of U.S. patent application Ser. No. 12/152,109, filed May 9, 2008, which claims priority to U.S. Provisional Application Ser. No. 60/928,946, filed May 11, 2007, entitled "MATERIAL PRODUCTION SYSTEM AND METHOD," all of which are hereby incorporated by reference as if their entire contents were set forth herein. The entire contents of U.S. patent application Ser. No. 11/110,341, filed on Apr. 19, 2005, entitled, "HIGH THROUGHPUT DISCOVERY OF MATERIALS THROUGH VAPOR PHASE SYNTHESIS" is incorporated by reference.

FIELD OF THE INVENTION

The present invention relates to catalysts, primarily metal catalysts used in fixed bed catalysis of fluid flows, and to methods of reusing catalytic materials. More particularly, the present invention relates to methods of producing a catalyst precursor material with nano-scale structure, methods of producing a skeletal catalyst with nano-scale structure from the precursor, and systems capable of performing these methods.

BACKGROUND OF THE INVENTION

Catalysts play many important roles in industry. One such role is fluid conditioning, including decontamination of flowing fluid. For example, a catalytic system might be employed to remove oxygen content from an inert gas flow. The "catalytic converter" employed in automobiles (circa. 2007 and earlier) removes certain pollutants from an exhaust flow produced by the engine. "Solid" catalysts—so-called because the catalytic compound exists in solid phase during use—are often employed in this role, as fluid decontamination typically involves removal of the contaminant from fluid phase, aerosol state, solution, or entrainment.

"Raney nickel", a solid phase catalyst formed of nickel grains bonded in a skeletal structure along with aluminum grains, performs many industrial roles, including fluid conditioning. A variety of similar catalysts employ other active materials, including iron or copper, instead of nickel, and other alloying components, such as zinc or silicon, instead of aluminum. Currently, all of these "Raney-style" catalysts are formed via processes essentially similar to the original recipe for Raney nickel.

A Raney-style process describes a multi-step method of forming a porous, active metal catalyst. First, a precursor is formed of at least a binary alloy of metals where one of the metals can be extracted. Second, the precursor is activated by extracting an alloy constituent leaving a porous residue comprising a metal that has catalytic activity. Such processes are described in, e.g. Raney, M. *Catalysts from Alloys*, Ind. Eng. Chem., 1940, 32, 1199; as well as U.S. Pat. Nos. 1,628,190; 1,915,473; 2,139,602; 2,461,396 and 2,977,327 to M. Raney. Commercial catalysts made by these type of processes are sold by W. R. Grace & Co. under the trademark RANEY® catalyst.

Often, additional materials are added and process parameters are varied to achieve a desired catalytic activity or function. Typically, the process parameters and additional materials included depend both on the active material employed and the catalytic function desired. Some added materials called "promoters" serve to enhance catalytic activity. A typical process parameter that is varied according to specific needs is the precursor alloy composition. For example, the precursor used for Raney nickel typically consists of equal amounts of nickel and aluminum by volume.

The traditional Raney-style process results in a collection of granular pieces, each with an internal porosity. Depending on their grain size, these particles are used in slurry or in packed-column systems as heterogeneous catalysts. Generally, larger particle sizes are required for use in packed-column systems. Traditionally, there is a tradeoff between surface area and particle size, with larger-sized particles having less surface area per unit volume. See, e.g. the background section of U.S. Pat. No. 4,895,994.

Although small powder catalysts have desirable surface area to volume characteristics, they are only suitable for batch processing and must be isolated after use. In order to avoid these disadvantages, a variety of processing regimes have been proposed to permit use of Raney particles in fixed-bed catalysis. For example, U.S. Pat. No. 4,895,994 describes a fixed bed catalyst shaped from Raney precursor mixed with a polymer, cured, and then activated via a leaching process. U.S. Pat. No. 5,536,694 describes a fixed-bed catalyst prepared from powders of Raney precursor mixed with a powder of its catalytically active component as a binder. However, these processes involve high sintering temperatures and thus cannot accommodate small, high surface-to-volume-ratio precursor particles (the sintering temperatures are sufficient to destroy the grain structure of the precursor alloy in small particles). Thus, lacking the high surface to volume ratio provided by the smallest precursor sizes, these approaches instead rely on macroporosity of the fixed bed structure to achieve high internal diffusion, making the most of their surface area.

Therefore, the smallest precursor particles suitable for fixed-bed catalyst production via traditional means are micron scale particles. FIG. 1 illustrates such a system process. Micron scale aluminum powder 112 and micron scale nickel powder 114 are combined in a melt-based alloying step 116, thereby producing nickel-aluminum alloy 118 in a variety of alloy phases. The nickel-aluminum alloy 118 is then processed and activated, such as by a leaching apparatus 120, resulting in a bulk porous structure 122 that is mostly nickel (though some aluminum may remain). In some prior art systems, the activation precedes a processing step, whereas in other systems, the activation follows processing to produce a bulk structure. In either case, an aluminum leach step 120 is involved in producing a bulk porous structure 122 composed substantially of nickel. Unfortunately, the smallest pores within the structure produced are micron scale.

What is needed in the art is a system and method for producing a catalyst precursor material and a skeletal catalyst having smaller particle size, and therefore larger surface area available for catalysis.

SUMMARY OF THE INVENTION

The embodiments of the present invention include methods of producing a catalyst precursor material with nano-scale structure, methods of producing a skeletal catalyst with nano-scale structure from the precursor, and systems capable of performing these methods.

In one aspect of the present invention, a method of producing a catalyst material with nano-scale structure is disclosed. The method comprises providing a starting powder into a nano-powder production reactor. The starting powder comprises a catalyst material. Next, the nano-powder production reactor nano-sizes the starting powder, thereby producing a nano-powder from the starting powder. The nano-powder comprises a plurality of nano-particles, with each nano-particle comprising the catalyst material. A catalyst precursor material is then formed from the nano-powder. This catalyst precursor material is a densified bulk porous structure comprising the catalyst material, wherein the catalyst material has a nano-scale structure.

In another aspect of the present invention, a method of producing a catalyst material with nano-scale structure from nickel and aluminum is disclosed. The method comprises providing a catalyst powder and a filler powder into a nano-powder production reactor. The catalyst powder comprises nickel, while the filler powder comprises aluminum. Next, a plasma flow is generated within the nano-powder production reactor and applied to the catalyst powder and the filler powder within the nano-powder production reactor, thereby nano-sizing the catalyst powder and the filler powder. As a result of this nano-sizing, a nano-powder is formed, which is defined by a plurality of nano-particles, wherein each nano-particle comprises nickel and aluminum. A catalyst precursor material is then formed from the nano-powder, wherein the catalyst precursor material is a densified bulk porous structure comprising the plurality of nano-particles.

In yet another aspect of the present invention, a method of producing a catalyst material with nano-scale structure purely from nickel is disclosed. The method comprises providing a catalyst powder into a nano-powder production reactor. The catalyst powder comprises nickel. Next, a plasma flow is generated within the nano-powder production reactor and applied to the catalyst powder within the nano-powder production reactor, thereby nano-sizing the catalyst powder. As a result of this nano-sizing, a nano-powder is formed, which is defined by a plurality of nano-particles, wherein each nano-particle comprises nickel. A catalyst precursor material is then formed from the nano-powder, wherein the catalyst precursor material is a densified bulk porous structure comprising the plurality of nano-particles.

In yet another aspect of the present invention, a system for producing a catalyst material with nano-scale structure is disclosed. The system comprises a powder dispensing device configured to provide a starting powder. The starting powder comprises a catalyst material. The system also comprises a nano-powder production reactor configured to receive the starting powder from the powder dispensing device and produce a nano-powder from the starting powder, wherein the nano-powder comprises a plurality of nano-particles, with each particle comprising the catalyst material. The system further includes a bonding device configured to receive the nano-powder and form a catalyst precursor material from the nano-powder, wherein the catalyst precursor material is a densified bulk porous structure comprising the catalyst material, and the catalyst material has a nano-scale structure.

In the systems and methods of the present invention, the catalyst material is preferably a metal of the transition group VIII of the periodic table of elements. Examples of preferred metals include nickel, iron, and cobalt. In some embodiments, the catalyst material is copper. Additionally, the filler material is preferably aluminum. However, in some embodiments, the filler material can be another material, such as zinc or silicon. Preferably, the starting powder is micron-scale, meaning it has an average grain size of at least 1 micron.

The systems and methods of the present invention involve forming a catalyst precursor material from nano-powder in such a way that leaves the nano-scale structure of the nano-powder substantially intact. In a preferred embodiment, the step of forming includes a step of bonding the nano-powder, possibly preceded by a step of pressing the nano-powder. Preferably, the bonding comprises spark-plasma sintering the nano-powder.

In some embodiments, the present invention can further comprise adding a promoter material to the bulk porous structure during the forming step. Preferably, the promoter material is one of the following: zinc, molybdenum, and chromium.

Furthermore, the present invention can include activating the catalyst material in the precursor in order to form a nano-skeletal catalyst. Different activation steps, such as leaching or etching, may be performed depending on the make-up and structure of the precursor. Both the oxide etching apparatus and the leaching apparatus preferably employ supercritical solutions. The oxide etching apparatus preferably employs a supercritical etch solution, while the leaching apparatus preferably employs a supercritical leaching solution. In certain embodiments where the use of leaching is appropriate, selective leaching with a basic solution is preferably used to remove the substantial portion of the filler material from the bulk structure. Preferably, the filler material left is present in a relatively stable alloy phase (e.g., the alloy phase is more stable than other alloy phases given the set of materials).

By forming the bulk structure from nano-sized particles instead of micron-sized (or larger sized) particles, the total catalytic surface area can be significantly increased, given that a nano-particle is significantly smaller than a micron particle thereby allowing for a greater quantity of nano-particles than micron particles. The present invention can increase the total catalytic surface area even more by removing a filler from each particle, thereby creating an internal porosity within each particle, rather than just the bulk porosity between the collection of particles. This internal porosity results in an internal surface area, and therefore, an increase in total surface area. The nano-skeletal structure produced via the present invention preferably has a surface area of at least 10,000 times the surface area of a micron scale structure of the same volume. The increase in surface area results in massive cost savings.

BRIEF DESCRIPTION OF THE DRAWINGS

FIG. 1 is a schematic illustration of a prior art system for producing a skeletal catalyst, specifically Raney nickel.

FIG. 2 is a schematic illustration of one embodiment of a system for producing a nano-scale skeletal precursor in accordance with the principles of the present invention.

DETAILED DESCRIPTION OF THE INVENTION

Figure 3:
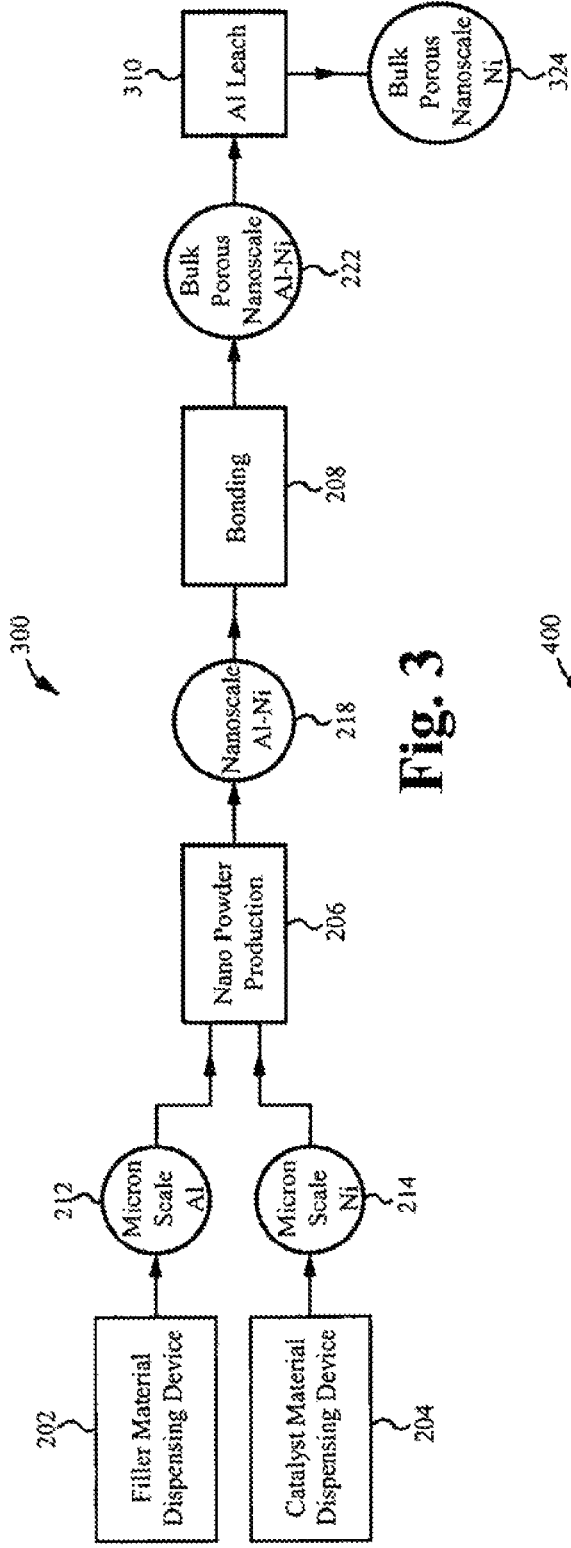
FIG. 3 is a schematic illustration of one embodiment of a system for producing a nano-scale skeletal catalyst in accordance with the principles of the present invention.

The description below concerns several embodiments of the invention. The discussion references the illustrated preferred embodiment. However, the scope of the present invention is not limited to either the illustrated embodiment, nor is it limited to those discussed, to the contrary, the scope should be interpreted as broadly as possible based on the language of the Claims section of this document.

This disclosure refers to both particles and powders. These two terms are equivalent, except for the caveat that a singular "powder" refers to a collection of particles. The present invention may apply to a wide variety of powders and particles. Additionally, for the purposes of this disclosure, the terms nano-powders and nano-particles refer to powders and particles having an average grain size less than 250 nanometers and an aspect ratio between one and one million.

The present invention will be readily understood by the following detailed description in conjunction with the accompanying drawings. To facilitate this description, like reference numerals designate like elements.

The embodiments of the present invention revolve around the use of a nano-powder production reactor to produce nano-skeletal catalytic precursors. In general, vapor phase nano-powder production means are preferred. Most preferably, the embodiments of the present invention use nano-powder production systems similar to those disclosed in U.S. patent application Ser. No. 11/110,341, filed on Apr. 19, 2005 and entitled, "HIGH THROUGHPUT DISCOVERY OF MATERIALS THROUGH VAPOR PHASE SYNTHESIS", which is currently published as U.S. Publication No. 2005-0233380-A. In such a nano-powder production system, working gas is supplied from a gas source to a plasma reactor. Within the plasma reactor, energy is delivered to the working gas, thereby creating a plasma. A variety of different means can be employed to deliver this energy, including, but not limited to, DC coupling, capacitive coupling, inductive coupling, and resonant coupling. One or more material dispensing devices introduce at least one material, preferably in powder form, into the plasma reactor. The combination within the plasma reactor of the plasma and the material(s) introduced by the material dispensing device(s) forms a highly reactive and energetic mixture, wherein the powder can be vaporized. This mixture of vaporized powder moves through the plasma reactor in the flow direction of the working gas. As it moves, the mixture cools and particles are formed therein. The still-energetic output mixture, comprising hot gas and energetic particles, is emitted from the plasma reactor. Following emission from the plasma reactor, the output mixture cools further and is exposed to a sampling device, which selectively samples portions of the output mixture, which comprises hot gas and particles of relatively homogeneous size distribution. Each particle can comprise a combination of the materials introduced by the material dispensing devices. The sampling device can be used to collect particles for further use or processing. It is contemplated that the sampling device can be incorporated into the reactor so that the reactor not only nano-sizes the powder, but samples and collects the nano-particles as well. In this respect, when discussing the nano-sizing and bonding steps below, it is implied that the nano-sizing step can include such particle sampling and collection necessary for providing the particles in sufficient form for the bonding step.

It is contemplated that other nano-powder production means, including non-vapor phase nano-powder production means, are within the scope of the present invention. Additionally, other configurations of sampling devices and collection devices are contemplated as being within the scope of the present invention as well.

Furthermore, the preferred embodiments of the present invention employ non-traditional sintering techniques to bond nano-scale materials in order to facilitate the preservation of the materials' nano-scale structure. Preferably, embodiments of the present invention employ fast sintering techniques to avoid agglomeration and loss of nano-structure. Exemplary fast sintering techniques are the sintering techniques known as spark-plasma sintering (SPS), field assisted sintering technique (FAST) or pulsed electric current sintering (PECS).

When used with conductive samples, such as in the present invention, these fast sintering techniques pulse DC current through the sample being sintered, causing resistive internal heating of the sample. Because the resistive load is relatively uniform throughout the sample, heat is generated uniformly throughout the sample. Furthermore, heat generation is initiated relatively simultaneously throughout a conductive sample, as it occurs with the electron movement. Since electron diffusion at the voltages involved is much faster than thermal diffusion, heating rates are potentially much faster than with conventional sintering. The fast heating and cooling provided by these techniques facilitates preservation of the sample's nano-scale structure.

Furthermore, embodiments of the present invention produce nano-scale bulk porosity, involving scales at which conventional liquid leaching chemistries can become less effective. Some embodiments contemplate using alternative leaching systems to remove filler materials. For example, supercritical fluid solutions are capable of wetting very small features. Thus, supercritical phase leaching chemistries are employed in some embodiments of the present invention.

FIG. 2 illustrates an embodiment of the present invention that is a system 200 for producing a catalyst precursor material with nano-scale structure. The system 200 includes a catalyst material dispensing device 204, a filler material dispensing device 202, a nano-powder production reactor 206, and a bonding device 208.

The catalyst material dispensing device 204 is configured to provide micron scale catalyst material 214. Preferably, the catalyst material of the present invention is a metal of the transition group VIII of the periodic table of elements. Examples of preferred metals include nickel, iron, and cobalt. In certain embodiments, copper can also be used as a catalyst material.

The filler material dispensing device 202 is configured to provide micron scale filler material 212. Preferably, the filler material of the present invention is aluminum. However, in some embodiments, the filler material can also be zinc or silicon.

In a preferred embodiment, the catalyst material dispensing device 204 and the filler material dispensing device 202 are fluidly coupled to a nano-powder production reactor 206. The nano-powder production reactor is configured to receive the catalyst material 214 and the filler material 212 and to produce a nano-powder 218 defined by a plurality of nano-particles, each particle comprising filler material and catalyst material, e.g. aluminum and nickel. This nano-sizing may be achieved in a variety of ways. However, in a preferred embodiment, the reactor employs the application of plasma to the powder as discussed above.

The bonding device 208 is configured to receive the nano-powder 218 and to form a densified bulk porous structure 222 from at least the nano-powder 218, employing means that leaves the nano-scale structure of the nano-powder substantially intact. Preferably, such means includes spark-plasma sintering. The bonding device 208 can be fluidly coupled to the nano-powder production reactor 206 in order to receive the nano-powder 218 from the reactor 206. Alternatively, the bonding device 208 can be separated from the reactor 206.

FIG. 3 illustrates an embodiment of the present invention that is a system 300 for producing a skeletal catalyst with nano-scale structure. The system 300 includes a portion similar to the system of FIG. 2 for producing a precursor with nano-scale structure. The system 300 includes a catalyst material dispensing device 204, a filler material dispensing device 202, a nano-powder production reactor 206, a bonding device 208, and a filler leaching apparatus 310.

Similar to FIG. 2, the catalyst material dispensing device 204 is configured to provide micron scale catalyst material 214, such as nickel. The filler material dispensing device 202 is configured to provide micron scale filler material 212, such as aluminum. In a preferred embodiment, the catalyst material dispensing device 204 and the filler material dispensing device 202 are fluidly coupled to a nano-powder production reactor 206.

The nano-powder production reactor is configured to receive the catalyst material 214 and the filler material 212 and to produce a nano-powder 218 defined by a plurality of nano-particles, each particle comprising filler material and catalyst material, e.g. aluminum and nickel. This nano-sizing may be achieved in a variety of ways. However, in a preferred embodiment, the reactor employs the application of plasma to the powder as discussed above.

The bonding device 208 is configured to receive the nano-powder 218 and to form a densified bulk porous structure 222 from at least the nano-powder 218, employing means that leaves the nano-scale structure of the nano-powder substantially intact. Preferably, such means includes spark-plasma sintering. The bonding device 208 can be fluidly coupled to the nano-powder production reactor 206 in order to receive the nano-powder 218 from the reactor 206. Alternatively, the bonding device 208 can be separated from the reactor 206.

The filler leaching apparatus 310 is configured to receive the bulk porous structure 222, preferably from the bonding device 208, and to remove a substantial portion of the filler material from the densified bulk porous structure 222 to form a nano-scale skeletal structure, thereby activating the material to form a nano-skeletal catalyst 324. Here, the filler leaching apparatus 310 removes substantially all of the filler material, leaving the nano-skeletal catalyst 324 to consist primarily of bulk porous nano-scale catalyst material. Although a very small amount of the filler material may remain, enough is removed to expose and activate pores in the catalyst material. In a preferred embodiment, selective leaching with a basic solution is used to remove the substantial proportion of the filler material from the bulk structure. Preferably, any remaining filler material is present in a relatively stable alloy phase (e.g., the alloy phase is more stable than other alloy phases given the set of materials).

Figure 4:
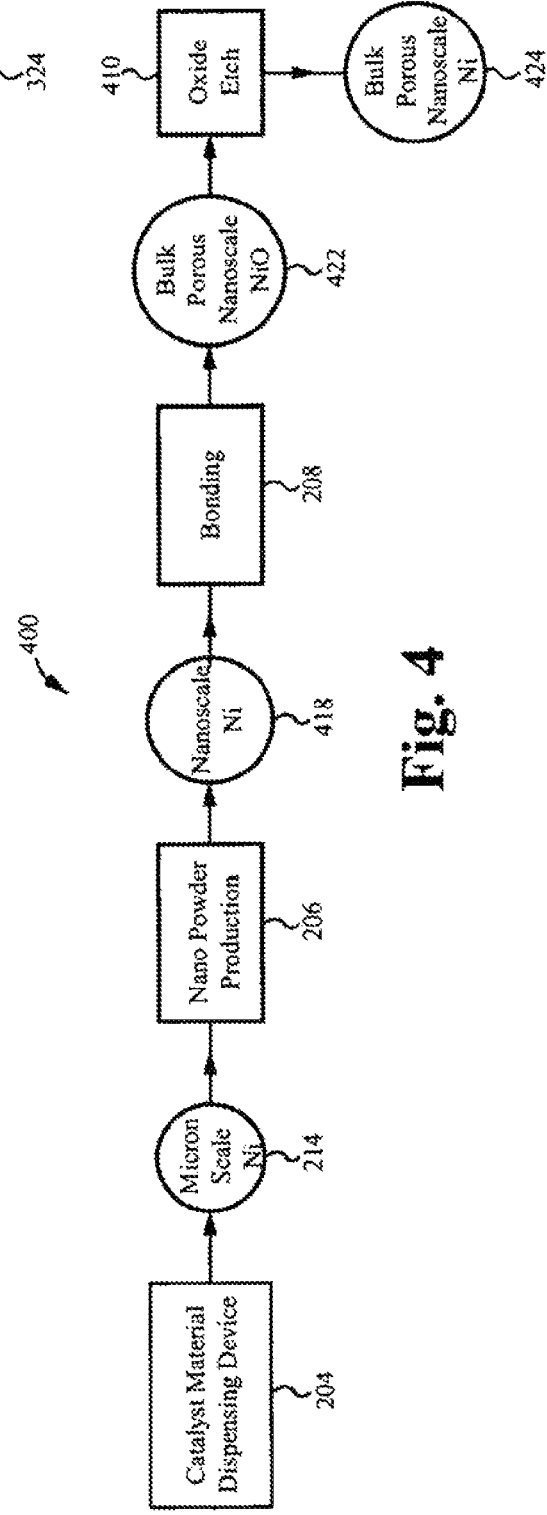
FIG. 4 is a schematic illustration of another embodiment of a system for producing a nano-scale skeletal catalyst in accordance with the principles of the present invention.

FIG. 4 illustrates an embodiment of the present invention that is a system 400 for producing a skeletal catalyst with nano-scale structure that does not require a filler material. The system 400 includes a catalyst material dispensing device 204, a nano-powder production reactor 206, a bonding device 208, and an oxide etching apparatus 410. In a preferred embodiment, system 400 operates under inert conditions.

Similar to FIGS. 2-3, the catalyst material dispensing device 204 is configured to provide micron scale catalyst material 214, such as nickel. In a preferred embodiment, the catalyst material dispensing device 204 is fluidly coupled to the nano-powder production reactor 206. This embodiment is characterized by an absence of filler material. Therefore, the only powder being provided to system 400 and reactor 206 is catalyst material.

The nano-powder production reactor 206 is configured to receive the catalyst material 214 and to produce a nano-powder 418 defined by a plurality of nano-particles, each particle comprising catalyst material, e.g. nickel. This nano-sizing may be achieved in a variety of ways. However, in a preferred embodiment, the reactor employs the application of plasma to the powder as discussed above.

The bonding device 208 is configured to receive the nano-powder 418 and to form a densified bulk porous structure 422 from the nano-powder 418, employing means that leaves the nano-scale structure of the nano-powder substantially intact. Preferably, such means includes spark-plasma sintering. The bonding device 208 can be fluidly coupled to the nano-powder production reactor 206 in order to receive the nano-powder 418 from the reactor 206. Alternatively, the bonding device 208 can be separated from the reactor 206.

Typically, the bonding process introduces some surface oxidation or other contamination into the bulk porous structure 422. Thus, the bonding step produces a contaminated bulk structure. Typically, this contamination is oxide. Here, the bulk porous structure 422 includes oxidized catalyst material, which in the present example is oxidized nickel. The oxide etching apparatus 410 is configured to receive the bulk porous structure 422, preferably from the bonding device 208, and to remove substantially all of the contamination from the densified bulk porous structure 422 in order to form a nano-scale skeletal structure, thereby activating the material to form a nano-skeletal catalyst 424. In the present example, the oxide leaching apparatus 410 removes substantially all of the oxide, leaving the nano-skeletal catalyst 424 to consist primarily of bulk porous nano-scale catalyst material. Although a very small amount of the contamination may remain, enough is removed to expose and activate the catalyst material.

FIGS. 2-4 illustrate systems capable of practicing embodiments of the present invention. These systems are configured to perform methods for producing nano-scale skeletal precursors and nano-scale skeletal catalysts.

Figure 5:
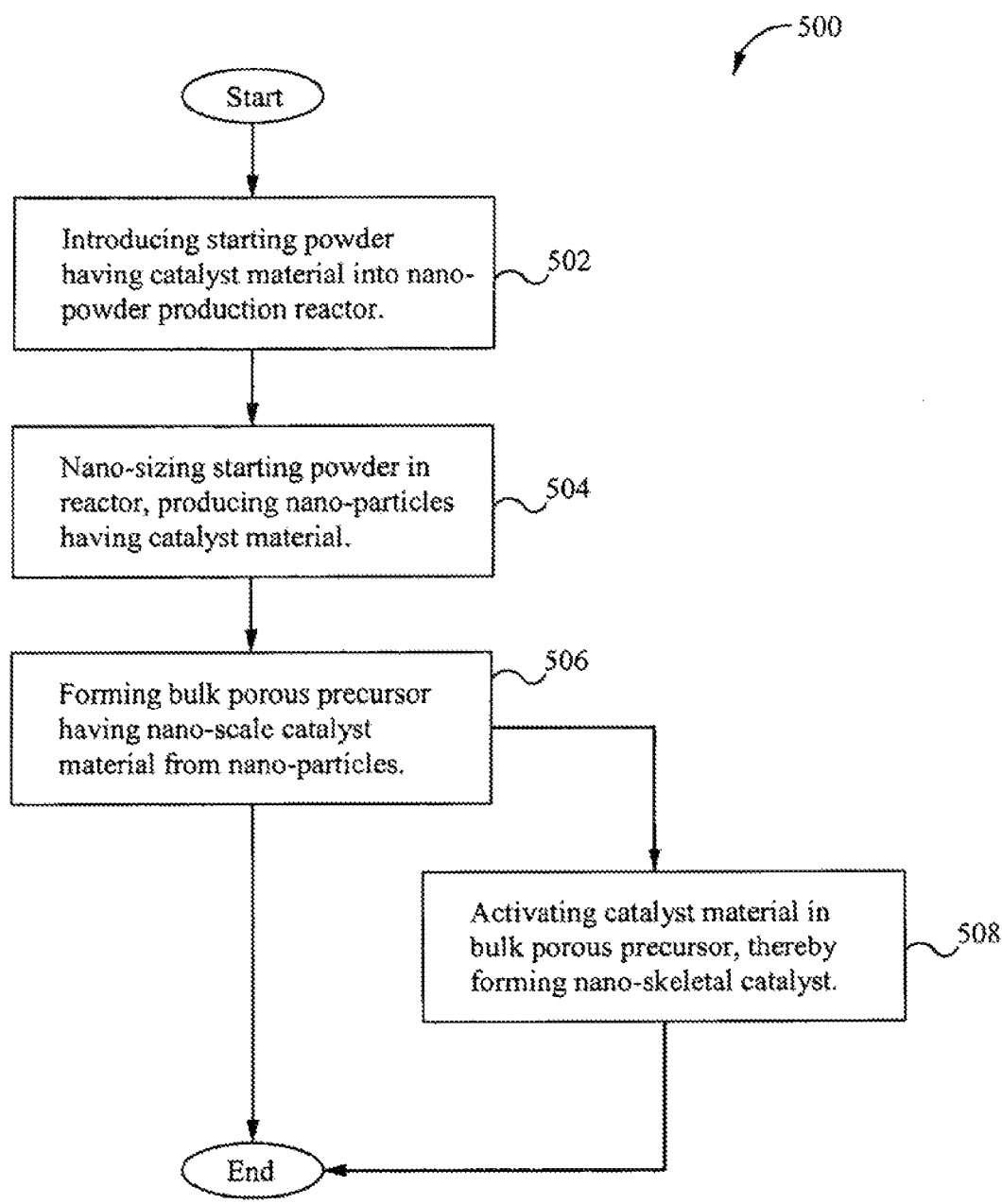
FIG. 5 is a flow chart illustrating one embodiment of a method of producing a nano-scale skeletal precursor and a nano-scale skeletal catalyst in accordance with the principles of the present invention.

FIG. 5 is a flow chart illustrating one embodiment of a method 500 of producing a nano-scale skeletal precursor and a nano-scale skeletal catalyst in accordance with the principles of the present invention.

At step 502, a starting powder is introduced into the nano-powder production reactor. This starting powder may contain both catalyst material and filler material, or only catalyst material.

At step 504, the reactor nano-sizes the starting powder, thereby producing a plurality of nano-particles, with each particle containing catalyst material. This nano-sizing may be achieved in a variety of ways. However, in a preferred embodiment, the reactor employs the application of plasma to the powder as discussed above.

At step 506, a densified bulk porous precursor is formed from the nano-particles. This densified precursor contains nano-scale catalyst material. The step of forming can include a step of pressing the nano-powder, followed by a step of bonding the nano-powder. However, it is contemplated that the densified bulk porous precursor may be formed in a variety of ways so long as the means that are employed leave the nano-scale structure of the nano-powder substantially intact. Preferably, such means comprises spark-plasma sintering.

If all that is desired is to form a densified bulk porous precursor, then the method 500 may come to an end. However, the method may optionally continue at step 508, where the catalyst material in the precursor is activated, thereby forming a nano-skeletal catalyst. Different activation steps, such as leaching or etching, may be performed depending on the make-up and structure of the precursor.

Figure 6:
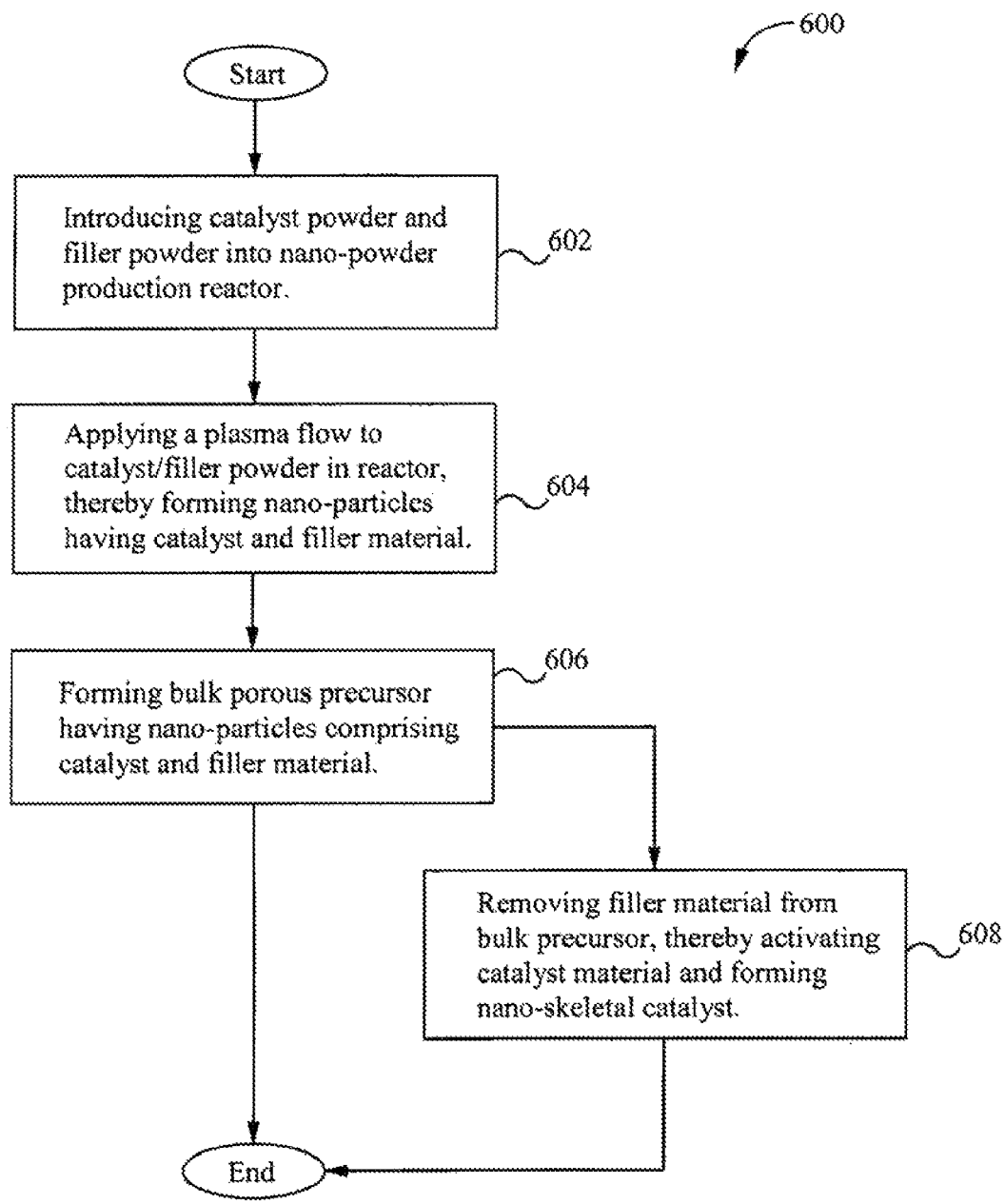
FIG. 6 is a flow chart illustrating one embodiment of a method of producing a nano-scale skeletal precursor and a nano-scale skeletal catalyst from a catalyst material and a filler material in accordance with the principles of the present invention.

FIG. 6 is a flow chart illustrating one embodiment of a method 600 of producing a nano-scale skeletal precursor and a nano-scale skeletal catalyst from a catalyst material and a filler material in accordance with the principles of the present invention.

At step 602, a starting powder is introduced into the nano-powder production reactor. This starting powder contains both catalyst material and filler material.

At step 604, the reactor applies a plasma flow to the staring powder, as discussed above, in order to nano-size the starting powder, thereby producing a plurality of nano-particles, with each particle containing catalyst material and filler material.

At step 606, a densified bulk porous precursor is formed from the nano-particles. This densified precursor contains nano-particles comprising the catalyst material and the filler material. The step of forming can include a step of pressing the nano-powder, followed by a step of bonding the nano-powder. However, it is contemplated that the densified bulk porous precursor may be formed in a variety of ways so long as the means that are employed leave the nano-scale structure of the nano-powder substantially intact. Preferably, such means comprises spark-plasma sintering.

If all that is desired is to form a densified bulk porous precursor, then the method 600 may come to an end. However, the method may optionally continue at step 608, where the catalyst material in the precursor is activated by removing substantially all of the filler material from the precursor, thereby forming a nano-skeletal catalyst. Different removal steps may be performed depending on the make-up and structure of the precursor. However, in a preferred embodiment, a leaching process is employed.

Figure 7:
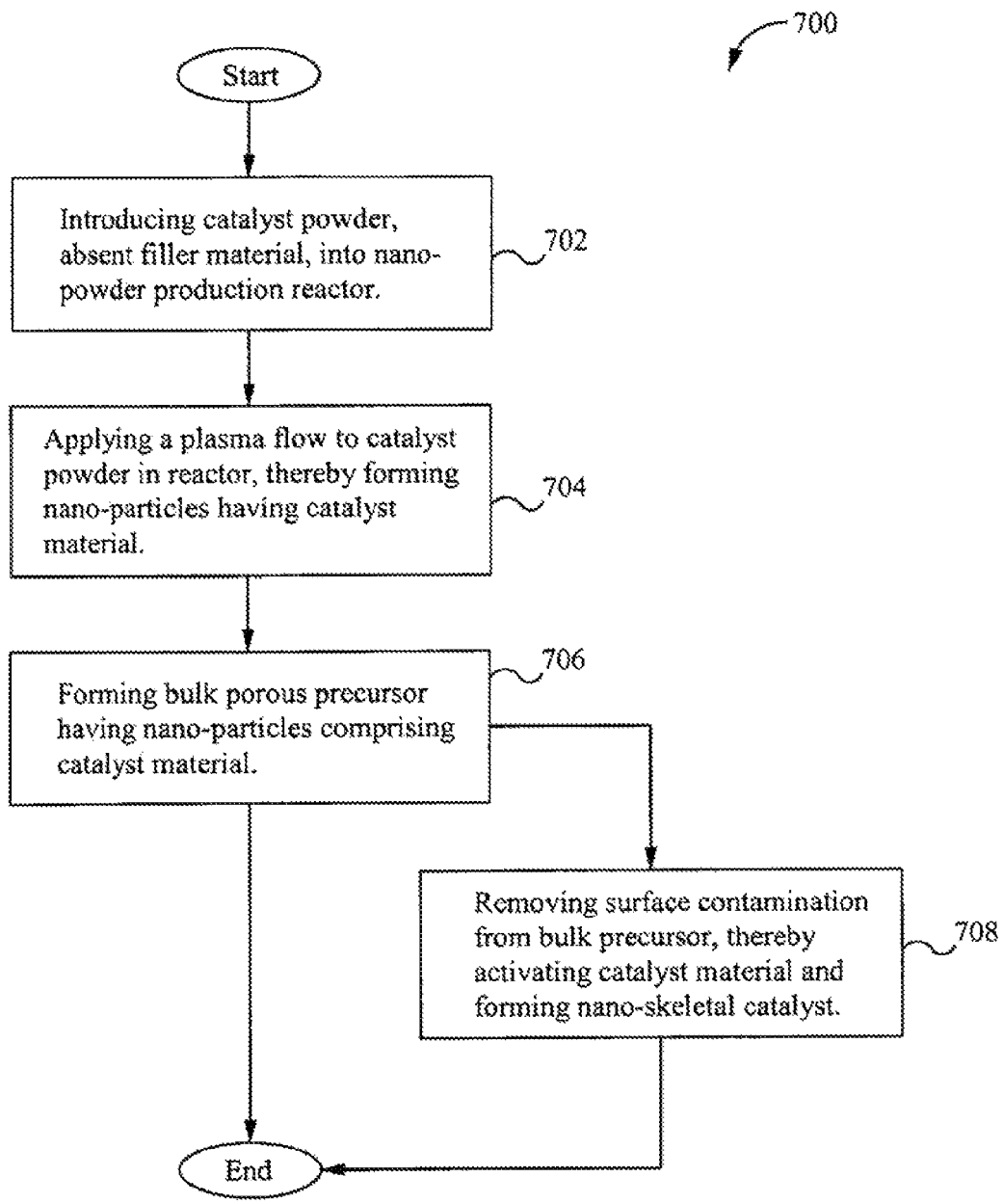
FIG. 7 is a flow chart illustrating one embodiment of a method of producing a nano-scale skeletal precursor and a nano-scale skeletal catalyst purely from a catalyst material in accordance with the principles of the present invention.

FIG. 7 is a flow chart illustrating one embodiment of a method 700 of producing a nano-scale skeletal precursor and a nano-scale skeletal catalyst purely from a catalyst material and without a filler material in accordance with the principles of the present invention.

At step 702, a starting powder is introduced into the nano-powder production reactor. This starting powder contains catalyst material and is characterized by the absence of filler material.

At step 704, the reactor applies a plasma flow to the starting powder, as discussed above, in order to nano-size the starting powder, thereby producing a plurality of nano-particles, with each particle containing catalyst material.

At step 706, a densified bulk porous precursor is formed from the nano-particles. This densified precursor contains nano-particles comprising the catalyst material. The step of forming can include a step of pressing the nano-powder, followed by a step of bonding the nano-powder. However, it is contemplated that the densified bulk porous precursor may be formed in a variety of ways so long as the means that are employed leave the nano-scale structure of the nano-powder substantially intact. Preferably, such means comprises spark-plasma sintering.

If all that is desired is to form a densified bulk porous precursor, then the method 700 may come to an end. However, the method may optionally continue at step 708, where the catalyst material in the precursor is activated by removing a substantial portion of any surface contamination from the precursor, thereby forming a nano-skeletal catalyst. Different removal steps may be performed depending on the make-up and structure of the precursor. However, in a preferred embodiment, an etching process is employed.

In some embodiments, the methods of the present invention can further comprise adding a promoter material to the bulk porous structure during the forming step. Preferably, the promoter material is one of the following: zinc, molybdenum, and chromium.

The embodiments of the present invention include methods of producing a catalyst precursor material with nano-scale structure, methods of producing a skeletal catalyst with nano-scale structure from the precursor, and systems capable of performing these methods. By forming the bulk structure from nano-sized particles instead of micron-sized (or larger sized) particles, the total catalytic surface area can be significantly increased, given that a nano-particle is significantly smaller than a micron particle thereby allowing for a greater quantity of nano-particles than micron particles. The present invention can increase the total catalytic surface area even more by removing a filler from each particle, thereby creating an internal porosity within each particle, rather than just the bulk porosity between the collection of particles. This internal porosity results in an internal surface area, and therefore, an increase in total surface area. The nano-skeletal structure produced via the present invention preferably has an effective BET surface area of at least 10,000 times the surface area of a micron scale structure of the same volume. The increase in surface area results in massive cost savings.

The present invention has been described in terms of specific embodiments incorporating details to facilitate the understanding of the principles of construction and operation of the invention. As such, references herein to specific embodiments and details thereof are not intended to limit the scope of the claims appended hereto. It will be apparent to those skilled in the art that modifications can be made to the embodiments chosen for illustration without departing from the spirit and scope of the invention.

What is claimed is:

1. A method of producing a catalyst material with nano-scale structure, the method comprising:
   providing a starting powder into a nano-powder production reactor, the starting powder comprising a catalyst material;
   nano-sizing the starting powder by using a plasma flow in the nano-powder production reactor, thereby producing a nano-powder from the starting powder, the nano-powder comprising a plurality of nano-particles, each nano-particle comprising the catalyst material;
   forming a catalyst precursor material from the nano-powder, wherein the catalyst precursor material is a densified bulk porous structure comprising the catalyst material, the catalyst material having a nano-scale structure, wherein the bulk porous structure of the catalyst precursor material further comprises a filler material; and
   further comprising removing a substantial portion of the filler material from the bulk structure of the catalyst precursor to form a nano-scale skeletal structure comprising the catalyst material, such that the catalyst material is activated to form a nano-skeletal catalyst.

2. The method of claim 1, wherein the step of nano-sizing the starting powder includes:
   generating the plasma flow within the nano-powder production reactor; and
   applying the plasma flow to the starting powder.

3. The method of claim 1, wherein the step of forming a catalyst precursor material includes pressing the nano-powder.

4. The method of claim 1, wherein the step of forming a catalyst precursor material includes bonding the nano-powder using spark plasma sintering, thereby preserving the nano-scale structure of the catalyst material.

5. The method of claim 1, wherein the starting powder has an average grain size greater than or equal to 1 micron.

6. The method of claim 1, wherein the catalyst material comprises a metal of the transition group VIII of the periodic table of elements.

7. The method of claim 6, wherein the metal comprises nickel.

8. The method of claim 6, wherein the metal comprises iron.

9. The method of claim 6, wherein the metal comprises cobalt.

10. The method of claim 1, wherein the filler material comprises aluminum.

11. The method of claim 1, wherein the filler material comprises zinc.

12. The method of claim 1, wherein the filler material comprises silicon.

13. The method of claim 1, wherein the step of removing the filler material is performed by using a leaching solution.

14. The method of claim 1, wherein the step of forming the catalyst precursor material includes adding a promoter material to the bulk porous structure, the promoter material comprising at least one of zinc, molybdenum and chromium.

15. The method of claim 1, wherein the starting powder consists only of the catalyst material.

16. The method of claim 15, wherein the step of nano-sizing the starting powder includes:
generating the plasma flow within the nano-powder production reactor; and
applying the plasma flow to the starting powder.

17. The method of claim 15, wherein the step of forming a catalyst precursor material includes pressing the nano-powder.

18. The method of claim 15, wherein the step of forming a catalyst precursor material includes bonding the nano-powder using spark plasma sintering, thereby preserving the nano-scale structure of the catalyst material.

19. The method of claim 15, wherein the starting powder has an average grain size greater than or equal to 1 micron.

20. The method of claim 15, wherein the step of forming the catalyst precursor material includes adding a promoter material to the bulk porous structure, the promoter material comprising at least one of zinc, molybdenum and chromium.

21. The method of claim 15, wherein the catalyst material comprises a metal of the transition group VIII of the periodic table of elements.

22. The method of claim 21, wherein the metal comprises nickel.

23. The method of claim 21, wherein the metal comprises iron.

24. The method of claim 21, wherein the metal comprises cobalt.

25. The method of claim 1, further comprising the step of removing surface contamination from the catalyst material.

26. The method of claim 25, wherein the step of removing the surface contamination is performed by using an etching solution.

27. The method of claim 1, wherein the starting powder comprises nickel.

28. The method of claim 27, wherein the step of forming a catalyst precursor material includes bonding the nano-powder using spark plasma sintering, thereby preserving the nano-scale structure of the nano-particles.

29. The method of claim 28, further comprising the step of removing surface contamination from the catalyst material.

30. The method of claim 27, further comprising:
providing a filler powder into the nano-powder production reactor, the filler powder comprising aluminum.

31. The method of claim 30, wherein the step of forming a catalyst precursor material includes bonding the nano-powder using spark plasma sintering, thereby preserving the nano-scale structure of the nano-particles.

32. The method of claim 31, further comprising removing a substantial portion of the aluminum from the bulk structure of the catalyst precursor material, thereby forming a nano-scale skeletal structure comprising the nickel, wherein the nickel is activated to form a nano-skeletal catalyst.

33. The method of claim 1, wherein the nano-powder production reactor is coupled to a sampling device such that the nano-powder is exposed to the sampling device as the nano-powder is emitted from the nano-powder production reactor.

34. The method of claim 1, wherein the nano-powder production reactor comprises one or more dispensing devices, each dispensing device coupled with a port that opens into the nano-powder production reactor.

* * * * *